United States Patent [19]

Pike et al.

[11] 3,931,284

[45] Jan. 6, 1976

[54] 11β-PGE$_2$ COMPOUNDS

[75] Inventors: John E. Pike; William P. Schneider, both of Kalamazoo, Mich.

[73] Assignee: The Upjohn Company, Kalamazoo, Mich.

[22] Filed: July 8, 1974

[21] Appl. No.: 486,374

Related U.S. Application Data

[63] Continuation-in-part of our co-pending application Ser. No. 71,390, filed Sep. 11, 1970, now abandoned.

[52] U.S. Cl. .......................... 260/468 D; 260/514 D
[51] Int. Cl.$^2$ .................. C07C 61/38; C07C 69/74
[58] Field of Search .................... 260/468 D, 514 D

[56] References Cited
OTHER PUBLICATIONS
Weinheimer et al., Tet. Letters, 5185 (1969).

*Primary Examiner*—Robert Gerstl
*Attorney, Agent, or Firm*—Morris L. Nielsen; Earl C. Spaeth

[57] ABSTRACT

Novel methods are disclosed for transforming PGA$_2$ and 15β-PGA$_2$ and their acetates, methyl esters, and acetate methyl esters to various prostanoic acids and esters of the PGE$_2$ and PGF$_{2\alpha}$ series. Some of the latter are novel and are useful for the same pharmacological purposes as PGE$_2$ and PGF$_{2\alpha}$.

3 Claims, No Drawings

11β-PGE₂ COMPOUNDS

CROSS REFERENCE TO RELATED APPLICATIONS

This application is a division of copending application Serial No. 403,094, filed October 3, 1973, issued as U.S. Patent 3,890,371, on June 17, 1975, which is a division of Serial No. 159,478, filed July 2, 1971, now issued as U.S. Patent 3,772,350, on November 13, 1973, which is a continuation-in-part of Serial No. 71,390, filed November 11, 1970, now abandoned.

DESCRIPTION OF THE INVENTION

This invention relates to novel compositions of matter, to novel methods for preparing them, and to novel intermediates used in those methods. This invention also relates to novel methods for preparing known compounds, and to novel intermediates used in those methods.

In particular, the several aspects of this invention relate to derivatives of prostanoic acid which has the following structure and numbering:

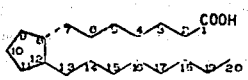
I

Some of the derivatives of prostanoic acid are known as prostaglandins. One of those, prostaglandin E₂ (PGE₂), has the following formula:

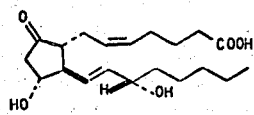
II

Another, prostaglandin F₂α (PGF₂α), has the formula:

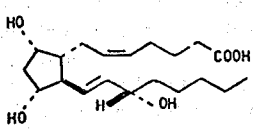
III

Still another, prostaglandin F₂β, (PGF₂β), has the formula:

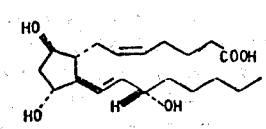
IV

In Formulas I to IV and in the formulas recited hereinafter in the specification and claims, broken line attachments to the cyclopentane ring indicate substituents in alpha configuration, i.e., below the plane of the cyclopentane ring.

The side-chain hydroxy at C-15 in Formulas II to IV is in S (alpha) configuration. That configuration is shown by attachment of side-chain hydroxy to C-15 with a dotted line and hydrogen with a heavy solid line. The alternative configuration for the side-chain hydroxy at C-15 is known as R or epi (beta), and is shown when necessary by attachment of said side-chain hydroxy to C-15 with a heavy solid line and hydrogen with a dotted line, thus

The prostaglandin corresponding to PGE₂ (Formula II) but with the R or epi configuration at C-15 will be designated 15β-PGE₂. See Nature, 212, 38 (1966) for discussion of the stereochemistry of the prostaglandins.

These conventions regarding formulas, names, and symbols for derivatives of prostanoic acid apply to the formulas, names, and symbols given hereinafter in the specification and claims. When reference is made hereinafter to the compounds of Formulas II to IV, by the symbols PGE₂, PGF₂α, or PGF₂β, or to the methyl esters of any of those, 15(S) configuration will be intended and by established custom, "S" or alpha will not be mentioned in the name or symbol. For all of the other compounds recited hereinafter, the configuration at C-15 will be identified in the name as "15β" whenever the 15(R) configuration is intended.

Molecules of the known prostaglandins each have several centers of asymmetry, and can exist in racemic (optically inactive) form and in either of the two enantiomeric (optically active) forms, i.e., the dextrorotatory and levorotatory forms. As drawn, Formulas II to IV each represent the particular optically active form of the prostaglandin which is obtained from certain mammalian tissues, for example, sheep vesicular glands, swine lung, or human seminal plasma, or by carbonyl and/or double bond reduction of a prostaglandin so obtained. See, for example, Bergstrom et al., Pharmacol. Rev. 20, 1 (1968) and references cited therein.

The several aspects of this invention relate to novel methods for preparing PGE₂, PGF₂α, and PGF₂β, their acetates and methyl esters, and the 15β-epimers of those compounds, to novel intermediates used in those methods, to novel methods used to make those intermediates, and to certain novel and pharmacologically useful analogs of PGE₂, PGF₂α, and PGF₂β.

The novel and pharmacologically useful PGE₂, PGF₂α, and PGF₂β analogs of this invention have the formulas:

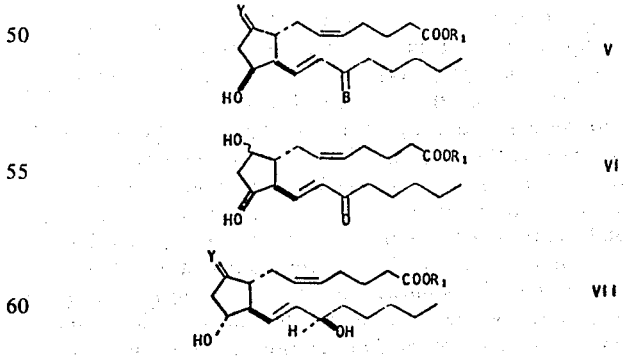

In Formulas V, VI, and VII, R₁ is hydrogen, alkyl of 1 to 8 carbon atoms, inclusive, cycloalkyl of 3 to 10 carbon atoms, inclusive, aralkyl of 7 to 12 carbon atoms, inclusive, phenyl, or phenyl substituted with one to 3 chloro or alkyl of one to 4 carbon atoms, inclusive.

Also encompassed by Formulas V, VI, and VII are pharmacologically acceptable salts when $R_1$ is hydrogen. In Formulas V and VII, Y is

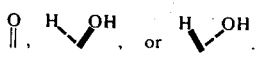

In Formula V, B is

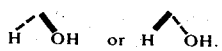

In Formula VI, ~ indicates attachment to the ring in alpha or beta configuration.

It will be observed that each of the novel compounds of Formulas V and VI has a hydroxy group attached to the 11-position in beta configuration. In $PGE_2$, $PGF_{2\alpha}$, and $PGF_{2\beta}$, and in the compounds of Formula VII, the hydroxy at C-11 is attached in alpha configuration.

With regard to Formulas V, VI, and VII, examples of alkyl of 1 to 8 carbon atoms, inclusive, are methyl, ethyl, propyl, butyl, pentyl, hexyl, heptyl, octyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by 1 to 3 chloro or alkyl of 1 to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

The known prostanoic acid derivatives, $PGE_2$, $PGF_{2\alpha}$, and $PGF_{2\beta}$, and their esters and pharmacologically acceptable salts are extremely potent in causing various biological responses. For that reason, these compounds are useful for pharmacological purposes. See, for example, Bergstrom et al., cited above, and references cited therein. A few of those biological responses are systemic arterial blood pressure lowering in the case of the $PGE_2$ and $PGE_{2\beta}$ compounds as measured, for example, in anesthetized (pentobarbital sodium) pentolinium-treated rats with indwelling aortic and right heart cannulas; pressor activity, similarly measured, for the $PGF_{2\alpha}$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the $PGE_2$ compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the $PGE_2$ compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the $PGE_2$ compounds, are useful in mammals, including man, as nasal decongestants. For this purpose, the compounds are used in a dose range of about 10 µg. to about 10 mg. per ml. of a pharmacologically suitable liquid vehicle or as an aerosol spray, both for topical application.

The PGE and $PGF_\alpha$ compounds are useful in the treatment of asthma. For example, these compounds are useful as bronchodilators or as inhibitors of mediators, such as SRS-A and Histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used one to four times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, ephedrine, etc.); xanthine derivatives (theophylline and aminophyllin); and corticosteroids (ACTH and predinisolone). Regarding use of these compounds see South African Pat. No. 681,055.

The $PGE_2$ compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The $PGE_2$, $PGF_{2\alpha}$, and $PGF_{2\beta}$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associates with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The $PGE_2$, $PGF_{2\alpha}$, and $PGF_{2\beta}$ compounds are especially useful as additives to blood, blood products, blood substitutes, and other fluids which are used in artificial extracorporal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The $PGE_2$ compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the $PGE_2$ compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The $PGE_2$ and $PGF_{2\beta}$ compounds are useful as hypotensive agents to reduce blood pressure in mammals, including man. For this purpose, the compounds are administered by intravenous infusion at the rate about 0.01 to about 50 μg. per kg. of body weight per minute, or in single or multiple doses of about 25 to 500 μg. per kg. of body weight total per day.

The $PGE_2$, $PGA_2$, and $PGF_{2\beta}$ compounds also increase the flow of blood in the mammalian kidney, thereby increasing volume and electrolyte content of the urine. Therefore, these compounds are useful in managing cases of renal disfunction, especially those involving blockage of the renal vascular bed. Illustratively, the compounds are useful to alleviate and correct cases of edema resulting, for example, from massive surface burns, and in the management of shock. For these purposes, the compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The $PGE_2$, $PGF_{2\alpha}$, and $PGF_{2\beta}$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started.

The $PGF_{2\alpha}$, $PGF_{2\beta}$, and $PGE_2$ compounds are useful for controlling the reproductive cycle in ovulating female mammals, including humans and animals such as monkeys, rats, rabbits, dogs, cattle, and the like. For that purpose, $PGE_2$ or $PGF_{2\alpha}$, for example, is administered systemically, e.g., intravenously, subcutaneously, and intravaginally, at a dose level in the range 0.001 mg. to about 20 mg. per kg. of body weight of the female mammal, advantageously during a span of time starting approximately at the time of ovulation and ending approximately at the next expected time of menses or just prior to that time. Additionally, expulsion of an embryo or fetus (abortion) is accomplished by similar administration of the compound during the first third of the normal mammalian gestation period.

As mentioned above, the $PGE_2$ compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The novel formula-V, -VI, and -VII $PGE_2$, $PGF_{2\alpha}$, and $PGF_{2\beta}$ analogs of this invention each cause the biological responses described above for $PGE_2$, $PGF_{2\alpha}$, and $PGF_{2\beta}$, respectively, and each of these novel compounds is accordingly useful for the above-described corresponding purposes, and is used for those purposes in the same manner as described above.

$PGE_2$, $PGF_{2\alpha}$, and $PGF_{2\beta}$, and their esters and pharmacologically acceptable salts are all potent in causing multiple biological responses even at low doses. For example, $PGE_2$ is extremely potent in causing vasodepression and smooth muscle stimulation, and is also potent as an antilipolytic agent. Moreover, for many applications, these known prostaglandins have an inconveniently short duration of biological activity. In striking contrast, the novel analogs of Formulas V, VI, and VII are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes because it has a different and narrower spectrum of biological activity than the known prostaglandins, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

The novel Formula-V, -VI, and -VII prostaglandin analogs are used as described above in free acid form in ester form, or in pharmacologically acceptable salt form. When the ester form is used, the alkyl esters are preferred, especially the alkyl esters wherein the alkyl moiety contains 1 to 4 carbon atoms, inclusive. Of those alkyl, methyl and ethyl are especially preferred for optimum absorption of the compound by the body or experimental animal system.

Pharmacologically acceptable salts of these prostaglandin analogs useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, these novel prostaglandin analogs are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility to use the free acid form or the pharmacologically acceptable salt form. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories, tampons, ring devices, and preparations adapted to generate sprays or foams or to be used for lavage, all prepared as known in the art, are used. For tissue implants, a sterile tablet or silicone rubber capsule or other object containing or impregnated with the substance is used.

The novel compounds of Formulas V, VI, and VII wherein $R_1$ is other than hydrogen, i.e., the esters wherein $R_1$ is alkyl or one to 8 carbon atoms, inclusive, cycloalkyl of 3 to 10 carbon atoms, inclusive, aralkyl of 7 to 12 carbon atoms, inclusive, phenyl, or phenyl substituted with one to 3 chloro or alkyl of one to 4 carbon atoms, inclusive, are prepared from the corresponding acids of Formulas V, VI, and VII, i.e., wherein $R_1$ is hydrogen, by methods known in the art. For example, the alkyl, cycloalkyl, and aralkyl esters are prepared by interaction of said acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively.

Esterification with diszohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389–394 (1954).

An alternative method for esterification of the carboxyl moiety of the novel PGr-type or PGE-type compounds of Formulas V, VI, and VII comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of the Formula-V, -VI, and -VII compounds are prepared by silylating the acid to protect the hydroxy groups, for example, replacing each —OH with —O—Si—$(CH_3)_3$. Doing that may also change —COOH to —COO—SI—Si—$3)_3$. A brief treatment of the silylated compound with water will change —COO—Si—$(CH_3)_3$ back to —COOH. Procedures for this silylation are known in the art and are discussed hereinafter. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—$(CH_3)_3$ are changed back to —OH by treatment with dilute acetic acid. Procedures for these transformations are known in the art.

The novel Formula-V, -VI, and -VII acids ($R_1$ is hydrogen) are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium salts, amine acid addition salts, and quaternary ammonium salts. The choice of procedure depends in part upon the solubility characteristics of the particular salt to be prepared. In the case of the inorganic salts, it is usually suitable to dissolve the acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt of the prostanoic acid derivative. Evaporation of the water or addition of a water-miscible solvent of moderate polarity, for example, a lower alkanol or a lower alkanone, gives the solid inorganic salt if that form is desired.

To produce an amine salt, the acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the acid with the stoichiometric amount of the corresponding quaternary ammonium hydroxide in water solution, followed by evaporation of the water.

The novel compounds of Formulas V, VI, and VII wherein $R_1$ is hydrogen or methyl, i.e., the free acids and the methyl esters, and also $PGE_2$, $PGF_{2\alpha}$, and $PGF_{2\beta}$, and the methyl esters of those are prepared by novel methods which are described hereinafter. For those methods, one of the following starting materials is used:

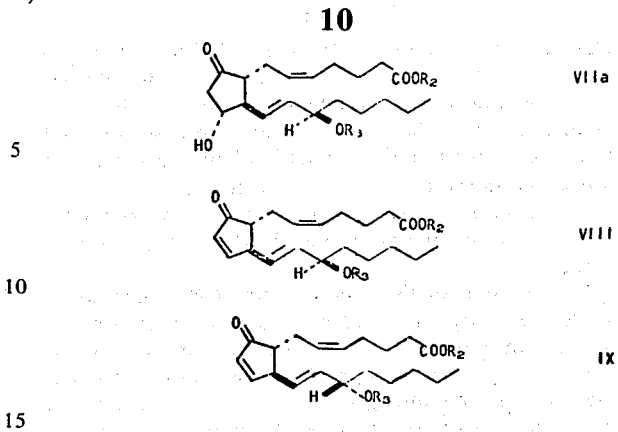

In Formulas VIIa, VIII, and IX, $R_2$ is either hydrogen or methyl, and $R_3$ is hydrogen or acetyl.

It will be observed that the compounds encompassed by Formula VIIa are also encompassed by VII. Thus, some Formula-VII compounds are useful both as intermediates and for pharmacological purposes.

These Formula-VIIa, -VIII, and -IX starting materials are all derivatives of prostanoic acid. The compounds of Formula VIII are known in the art or are available by methods known in the art. See, for example, Weinheimer et al., Tetrahedron Letters, No. 59, 5185 (1969); H. W. Youngken, Jr. (ed), "Food-Drugs from the Sea", Proc. Marine Technology Society, pp. 311–314 (1969). The Formula-VIII compound wherein $R_2$ and $R_3$ are both hydrogen is designated 15$\beta$-$PGA_2$, alternatively 15(R)-$PGA_2$ or 15-epi-$PGA_2$. The other compounds encompassed by Formula VIII are designated 15$\beta$-$PGA_2$ acetate, 15$\beta$-$PGA_2$ methyl ester, and 15$\beta$-$PGA_2$ acetate methyl ester.

The compounds of Formula VIIa are new in the art and methods for preparing them are described hereinafter. The Formula-VIIa compound wherein $R_2$ and $R_3$ are both hydrogen is designated 15$\beta$-$PGE_2$, alternatively 15(R)-$PGE_2$ or 15-epi-$PGE_2$. The other compounds encompassed by Formula VIIa are designated 15$\beta$-$PGE_2$ 15-acetate, 15$\beta$-$PGE_2$ methyl ester, and 15$\beta$-$PGE_2$ acetate methyl ester.

The compounds of Formula IX are known in the art. See, for example, British patent specification No. 1,097,533. Novel methods for preparing these Formula-IX compounds are described hereinafter. The Formula-IX compound wherein $R_2$ and $R_3$ are hydrogen is designated $PGA_2$. The other compounds encompassed by Formula IX are designated $PGA_2$ acetate, $PGA_2$ methyl ester, and $PGA_2$ acetate methyl ester.

All of the compounds of Formulas VIIa, VIII, and IX are obtained by extraction from a marine invertebrate. The compounds of Formula VIIa and VIII, i.e., the 15$\beta$ compounds, are obtained from colonies of Plexaura homomalla (Esper), 1792, forma R. The compounds of Formula IX, i.e., the 15(S) or alpha compounds, are obtained from colonies of Plexaura homomalla (Esper), 1792, forma S.

These Plexaura homomalla forms are members of the subclass Octocorallia, order Gorgonacea, suborder Holaxonia, family Plexauridae, genus Plexaura. See, for example, Bayer, "The Shallow-Water Octocorallia of the West Indian Region", Martinus Nijhoff, The Hague (1961). Colonies of these Plexaura homomalla forms are abundant on the ocean reefs in the zone from the low-tide line to about 25 fathoms in the tropical and subtropical regions of the western part of the Atlantic Ocean, from Bermuda to the reefs of Brazil, including the eastern shore reefs of Florida, the Caribbean island and mainland reefs, and the Gulf of Mexico island and mainland reefs. These colonies are bush-like or small tree-like in habit, and are readily identified for collection as *Plexaura homomalla* (Esper), 1792, by those of ordinary skill in this art. Forms R and S are distinguished by the methods described in Preparation 1 below.

The colonies of these two forms of *Plexaura homomalla* are easily separated into an outer bark-like cortex and an inner wiry proteinaceous stem or skeleton. Symbiotic algae or Zooxanthellae are also present in the colonies. Weinheimer et al., cited above, disclose the occurence of the Formula-VIII compounds wherein $R_2$ and $R_3$ are both hydrogen and wherein $R_2$ is methyl and $R_3$ is acetyl in the air dried cortex of "*Plexaura homomalla* (Esper)".

The choice of isolation or extraction method is determined by the particular Formula-VIIa, -VIII, or -IX compound desired. Maximum yield of the Formula-VIII or -IX diester is realized by freezing whole or coarsely cut or chopped fresh *Plexaura homomalla* colonies within an hour and preferably sooner after the colonies are removed from the reef. For small scale collections, this freezing is done advantageously by contacting the colonies or pieces with solid carbon dioxide. For larger scale collections, other suitable freezing methods are known to the art. The frozen colonies or colony pieces should be kept frozen, preferably below about $-20°$ C. until the extraction takes place.

The major component of fresh *Plexaura homomalla* (Esper), 1792, forma R is $15\beta$-$PGA_2$ acetate methyl ester, the Formula-VIII compound wherein $R_2$ is methyl and $R_3$ is acetyl. Relatively minor components are the hydroxy methyl ester, the acetate, and the hydroxy acid of Formula VIII and the $15\beta$-$PGE_2$ compounds encompassed by Formula VIIa. Of the latter, the $15\beta$-$PGE_2$ acetate methyl ester ($R_2$ is methyl and $R_3$ is acetyl) is the most abundant. The major component of *Plexaura homomalla* (Esper), 1792, forma S is $PGA_2$ acetate methyl ester, the Formula-IX compound wherein $R_2$ is methyl and $R_3$ is acetyl. Relatively minor components are the hydroxy methyl ester, the acetate, and the hydroxy acid of Formula IX, and the $PGE_2$ compounds corresponding to Formula VIIa but having the 15(S) configuration.

When the acetate methyl ester compound of Formula VIIa, VIII, or IX ($R_2$ is methyl, $R_3$ is acetyl) is desired as a starting material, a suitable method comprises grinding the frozen whole *Plexaura homomalla* colonies or colony pieces, advantageously in a hogger to a particle size with the largest dimension about 5 mm., and then extracting the resulting particles with any of the usual organic solvents, preferably one with moderate to high polarity, e.g., dichloromethane or methanol, advantageously, for 15 to 30 minutes in a high speed mixer. The desired compounds are isolated from the extract by evaporation, and then chromatography of the resulting residue. By this procedure, about 24 g. of $15\beta$-$PGA_2$ acetate methyl ester, and about one g. each of $15\beta$-$PGA_2$ methyl ester and $15\beta$-$PGE_2$ are obtained by dichloromethane extraction of 1500 g. of frozen *Plexaura homomalla* (Esper), 1792, forma R colonies or colony pieces. Similarly, relatively large amounts of $PGA_2$ acetate methyl ester are obtained from frozen *Plexaura homomalla* (Esper), 1792, forma S.

When the 15-hydroxy methyl ester of Formula VIIa, VIII, or IX ($R_2$ is methyl, $R_3$ is hydrogen) is desired as a starting material, a suitable method comprises grinding the frozen whole *Plexaura homomalla* colonies or colony pieces as above, and then contacting the resulting particles with a lower alkanol, preferably methanol or ethanol, at 25° C. for several days. The solvent is then evaporated and the residue chromatographed to give substantially larger amounts of the hydroxy methyl ester compound relative to the acetate methyl ester compound. When the contact between the *Plexaura homomalla* particles and the alkanol is substantially shorter, substantially the same amount and ratio of the various Formula-VIIa, -VIII, or -IX compounds is obtained with the alkanol as with dichloromethane. An alternative method for obtaining these 15-hydroxy methyl esters is described below.

When $15\beta$-$PGA_2$, $15\beta$-$PGE_2$, or $PGA_2$ ($R_2$ and $R_3$ in Formulas VIIa, VIII, and IX are both hydrogen) are desired as starting materials in the novel processes of this invention, they are prepared from the corresponding methyl esters and 15-acetate methyl esters after those have been extracted from the *Plexaura homomalla* colonies or colony pieces as described above. A suitable method for removing the acetyl group of each of the Formula-VIIa, -VIII, and -IX 15-acetate methyl esters comprises mixing the acetate methyl ester in lower alkanol solution, preferably in methanol solution, with a strong acid, e.g., perchloric acid, for about 15 hours at 25° C. A suitable method for removing the methyl group of any of the Formula-VIIa, -VIII, and -IX methyl esters is the enzymatic hydrolysis described in West Germany Offenlegungschrift No. 1,937,912, reprinted in Farmdoc Complete Specifications, Book No. 14, No. 6869R, Week $R_5$, March 18, 1970.

Another method for obtaining $15\beta$-$PGA_2$, $15\beta$-$PGE_2$, or $PGA_2$ from *Plexaura homomalla* colonies or colony pieces comprises freezing the *Plexaura homomalla* colonies or colony pieces, preferably at a temperature below about $-20°$ C., and then allowing the colonies or colony pieces to thaw and warm to a temperature in the range 20° to 30° C. The thawed colonies or colony pieces are then maintained in the range 20° to 30° C. for at least 24 hours. After that treatment, substantially none of the Formula-VIIa, -VIII, and -IX compounds wherein $R_2$ is methyl and $R_3$ is acetyl are present, the principal Formula-VIIa, -VIII, and -IX compounds present being those wherein $R_2$ and $R_3$ are both hydrogen, the minor components being those wherein $R_2$ is methyl and $R_3$ is hydrogen or wherein $R_2$ is hydrogen and $R_3$ is acetyl. As before, Formula-VIIa and -VIII compounds are obtained from colonies of *Plexaura homomalla* (Esper), 1792, forma R, and Formula-IX compounds are obtained from colonies of *Plexaura homomalla* (Esper), 1792, forma S.

A preferred procedure for the $PGA_2$ and $PGE_2$ type free acids comprises grinding the *Plexaura homomalla* colonies or colony pieces, preferably to a particle size with the largest dimension about 5 mm., and then maintaining the mixture in contact with water at a temperature in the range 20° to 30° C. for at least 24 hours. This mixture is filtered, and the filtrate is extracted with an appropriate water-immiscible solvent, e.g., ethyl acetate. The solid residue is also extracted with an appropriate solvent, e.g., methanol. The two extracts are evaporated, and the total residue is chromatographed to give Formula-VIIa and -VIII or Formula-IX compounds, the principal component in each case being the compound wherein $R_2$ and $R_3$ are both hydrogen.

Since our invention of the novel processes for transforming $PGA_2$ and $15\beta$-$PGA_2$ and their methyl esters and acetate methyl esters to the various prostanoic acids and esters disclosed herein, it has now been found that small amounts of the 5,6-trans compounds of $PGA_2$ and $15\beta$-$PGA_2$ and their methyl esters and acetate methyl esters are also obtained from *Plexaura homomalla* (Esper), 1792, forms R and S. These 5,6-Trans compounds are extracted with and accompany the corresponding $PGA_2$-type compounds through many of their transformations. For example, $PGA_2$ containing 5,6-trans-$PGA_2$ yields a mixture of $PGE_2$ and 5,6-trans-$PGE_2$ by the process represented in Chart E below.

When it is desired, for pharmacological purposes, to prepare the major products of this invention free of 5.6-trans compounds, those 5,6-trans compounds are separated either from the starting reactants or from the products. In either case, several methods are available for separating the 5,6-trans-$PG_2$ compounds from the $PG_2$ compounds. One method is by means of a silver-saturated ion-exchange resin (for example, see E. A. Emken et al., J. Am. Oil Chemists' Soc. 41, 388 (1964)), illustrated below in Preparations 5 and 6. The other method is by preferentially forming a mercuric acetate adduct of the 5,6-cis compound which is extractable into polar solvents illustrated below in Preparation 7.

Following the processes discussed herein and the procedures of the Examples below, the 5,6-trans-PG (and -15$\beta$-$PG_2$) compounds are transformed to other 5,6-trans-$PG_2$ (and -15$\beta$-$PG_2$) compounds, e.g., 5,6-trans-$PGA_2$ to 5,6-trans-$PGE_2$, 5,6-trans-15$\beta$-$PGA_2$ acetate methyl ester to 5,6-trans-15$\beta$-$PGF_{2\alpha}$ acetate methyl ester, and the like.

As mentioned above, the Formula-VIIa, -VIII, and -IX compounds are starting materials for the preparation of $PGE_2$, $PGF_{2\alpha}$, and $PGF_{2\beta}$, the methyl esters of those, and also the novel compounds of Formulas V and VI, and some of the novel compounds of Formula VII. The novel processes using these starting materials will now be described.

The Formula-VIII and -IX starting materials are both of the PGA-type. According to the novel processes of this invention, those are first transformed to corresponding PGE-type compounds. The chemical reactions involved in those transformations are shown generically in Chart A.

In Chart A, $R_4$ is hydrogen, methyl, or $-Si-(A)_3$ wherein A is alkyl of one to 4 carbon atoms, inclusive, aralkyl of T to 12 carbon atoms, inclusive, phenyl, or phenyl substituted with one or 2 fluoro, chloro, or alkyl of one to 4 carbon atoms, inclusive; G is

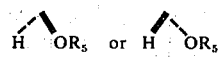

wherein $R_5$ is hydrogen, acetyl, or $-Si-(A)_3$ when $R_4$ is hydrogen or methyl, and $R_5$ is $-Si(A)_3$ when $R_4$ is $-Si-(A)_3$; $R_2$ is hydrogen or methyl; and B is

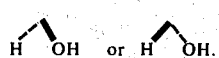

Thus, Formula X in Chart A encompasses the starting materials of Formulas VIII and IX obtained from *Plexaura homomalla*, and also compounds of the formula:

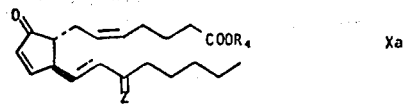

wherein $R_4$ is as defined above, and Z is

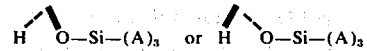

wherein A is as defined above.

In Formula XI, of Chart A,

indicates attachment of the epoxy oxygen to the ring in alpha or beta configuration. In Formulas XII and XIII of Chart A, ~ indicates attachment of hydroxy to the ring in alpha or beta configuration.

CHART A

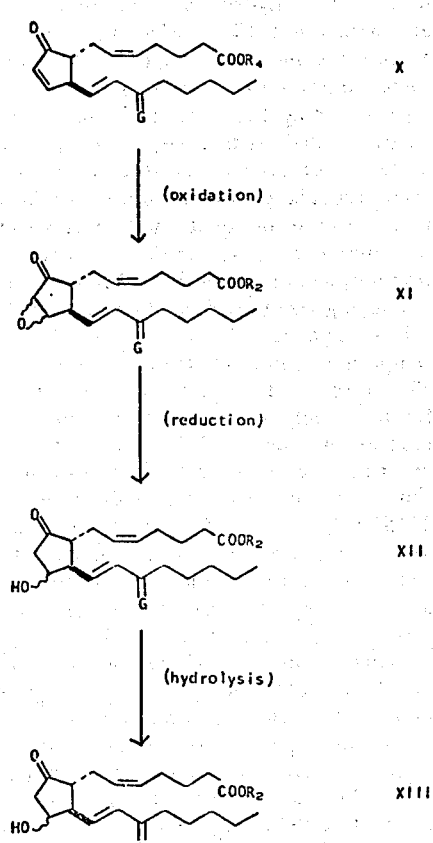

It will be observed in Chart A that the Formula-XII and -XIII products each encompass four stereoisomeric groups of compounds. Included are compounds with the 11$\alpha$, 15(S) configuration of $PGE_2$ (Formula II, above), compounds with the configuration of 11$\alpha$, 15$\beta$-$PGE_2$ (Formula VIIa) as obtained from *Plexaura*

*homomalla* (Esper), 1792, forma R, and both the 15(S) and 15(R) compounds with the 11β configuration of the novel Formula-V compounds of this invention wherein Y is

i.e., 11β-PGE$_2$ and 11β,15β-PGE$_2$. If the Formula-XII or -XIII product is to have the 15(S) configuration, e.g., PGE$_2$ or 11β-PGE$_2$, then the Formula-X starting material should have the 15(S) configuration, i.e., G should be

If a 15β compound of Formula XII or XIII is desired, e.g., 15β-PGE$_2$ or 11β,15β-PGE$_2$, then the Formula-X starting material should have the 15(R) or 15-epi configuration, i.e., G should be

As described above, Formula-IX starting materials wherein R$_2$ is hydrogen or methyl and R$_3$ is hydrogen, and with the 15(S) configuration, are obtained from *Plexaura homomalla* (Esper), 1792, forma S. Those same compounds are also produced by reacting the corresponding 15(R) (beta) compound with a hydrocarbyl or halohydrocarbyl sulfonyl chloride or bromide, preferably a lower alkylsulfonyl chloride or bromide, especially methanesulfonyl chloride or bromide, or a benzene- or substituted-benzenesulfonyl chloride or bromide, e.g., p-toluenesulfonyl chloride. This reaction is done in the presence of at least sufficient tertiary amine, e.g., triethylamine, to absorb the hydrogen chloride or hydrogen bromide by-product, and at a low temperature, preferably in the range −15° to +15° C. The presence of an inert liquid diluent, e.g., tetrahydrofuran, is helpful to maintain a mobile homogenous reaction mixture. At 0° C. and with methanesulfonyl chloride, usually 30 to 60 minutes is a sufficient reaction time. The product is hydrolyzed to a mixture of 15(S) (alpha) and 15(R) hydroxy compounds. These are separated by procedures known in the art, and the 15(S) product is purified by procedures known in the art, advantageously by chromatography on silica gel. This reaction is also used to transform 15(S) Formula-IX starting materials wherein R$_2$ is hydrogen or methyl and R$_3$ is hydrogen to the corresponding 15(R) compounds. In each case, a mixture of 15(R) product and 15(S) starting material is obtained, the components of which are separated as described above.

Another method of transforming a 15β-PG compound to a PG compound is by converting it to a mixture of PG 15-formate nad 15β-PG 15-formate compounds, separating the PG 15-formate, and hydrolyzing the PG 15-formate to the desired PG compound (see J.E. Pike et al., J. Org. Chem. 34, 3552 (1969)).

The mixture of alpha and beta 15-formates is prepared by maintaining the 15β compound, e.g. 15β-PGE$_2$, 15β-PGA$_2$, or 15β-PGF$_2$ $\alpha$, in formic acid buffered with an alkali metal formate in the range 10° to 50° C. until a substantial amount of the 15β compound, e.g. 15β-PGE$_2$ 15-formate, has been transformed to the PG 15-formate. The mixture of the PG 15-formate and 15β 15-formates thus obtained is then separated by known methods, e.g. by chromatography.

The PG 15-formate can then be hydrolyzed to the desired PG 15-hydroxy compound. The 15β-PG 15-formate yields the corresponding 15β-PG 15-hydroxy compound, which is then recycled through the above steps for further isomerization to the PG compound if desired.

This procedure is also useful to transform a PG compound to a 15β PG compound, by obtaining a mixture of the intermediate PG 15-formate and 15β-PG 15-formate compounds, separating them, and hydrolyzing them to the respective PG 15-hydroxy and 15β-PG 15-hydroxy compounds. In this case, the PG compound is recycled for further isomerization to the 15β compound.

Referring again to Chart A, the transformation of starting material X to epoxide XI is carried out by reacting X with any agent known to epoxidize an αβ-unsaturated ketone without reacting with isolated carbon-carbon double bonds, for example see Steroid Reactions, Carl Djerassi, ed., Holden-Day Inc., 1963, p. 593. Especially preferred are aqueous hydrogen peroxide or an organic tertiary hydroperoxide. See, for example, Organic Peroxides, A.V. Tobolsky et al., Interscience Publishers, N.Y., 1954. For this purpose, the peroxide or hydroperoxide is employed in an amount of at least one equivalent per mole of Formula-X reactant in the presence of a strong base, e.g., an alkali metal hydroxide, a metal alkoxide, or a quaternary ammonium hydroxide. For example, there is employed lithium hydroxide, sodium hydroxide, potassium hydroxide, lithium ethoxide, lithium octyloxide, magnesium methoxide, magnesium isopropoxide, benzyltrimethylammonium hydroxide, tetraethylammonium hydroxide, butyltrimethylammonium hydroxide, butyldiethylphenylammonium hydroxide, benzylethyldimethylammonium hydroxide, benzyldimethyloctadecylammonium hydroxide, benzyldodecyldimethylammonium hydroxide, decyldimethylphenylammonium hydroxide, and the like. See, for example, Sidgwick, Organic Chemistry of Nitrogen, Third Edition, rev. by Miller and Springall, Oxford, 1966, pp. 116–127.

The ratio of alpha to beta epoxide formed in the reaction is related to four factors: the epoxidizing agent, the base, the diluent, and the temperature. Hydrogen peroxide is employed in the concentrations usually available, for example 3% to 90%, although 30% is especially convenient. When the alpha epoxide is the desired product, tert-butyl hydroperoxide is especially preferred as the epoxidizing agent. Examples of other organic tertiary hydroperoxides useful for this purpose are tert-pentyl hydroperoxide, decahydronaphthyl hydroperoxide, α,α-dimethylbenzyl hydroperoxide, and 1,1-diphenylethyl hydroperoxide. The base is present in the proportion of 0.1–3.0, preferably about 0.1–0.5 equivalent of base per mole of starting material X when R$_4$ is methyl and R$_5$ is acetyl; preferably about 1.5–2.5 equivalent of base per mole of starting material VIII or IX wherein R$_2$ and R$_3$ are hydrogen. When the alpha epoxide is the desired product, lithium hydroxide, lithium or magnesium alkoxides of 1 to 8 carbon atoms, and benzyltrimethylammonium hydroxide are the preferred bases, although the lithium and magnesium compounds are especially preferred.

It is advantageous to use an inert liquid diluent in the epoxidation step to produce a mobile homogenous reaction mixture, for example, a lower alkanol, dioxane, tetrahydrofuran, dimethoxyethane, dimethylsulfoxide, or dimethylsulfone. When the alpha epoxide is preferred, tetrahydrofuran or the less polar dimethoxyethane are especially preferred as the diluent. A reaction temperature in the range −60° to 0° C. is generally preferred, especially below −10° C. The lower temperatures below −30° C. are especially preferred for favoring formation of alpha epoxide over beta epoxide. At a temperature of −20° C., the epoxidation is usually complete in 3 to 6 hours. It is also preferred that the reaction be carried out in an atmosphere of an inert gas, e.g., nitrogen, helium, or argon. When the reaction is complete as shown by the absence of starting material on TLC plates (3% acetone in dichloromethane), the reaction mixture is neutralized, and the epoxy product is isolated by procedures known in the art, for example, evaporation of the diluent and extraction of the residue with an appropriate water-immiscible solvent, e.g., ethyl acetate.

This transformation of X to XI usually produces a mixture of Formula-XI alpha and beta epoxides both with either the 15(R) or 15(S) configuration depending on the configuration at C-15 in the Formula-X starting material. Although these mixtures are separated into the individual alpha and beta isomers, for example, by chromatography by procedures known to be useful for separating alpha and beta epoxide mixtures, it is usually advantageous to transform the Formula-XI mixture of alpha and beta epoxides to the corresponding mixture of Formula-XII IIα and IIβ hydroxy compounds. The latter mixture is then readily separated into the IIα and IIβ compounds, for example, by chromatography of silica gel.

During the transformation of epoxides XI to alcohols XII, an alpha epoxide yields an IIα-hydroxy compound, and a beta epoxide yields an IIβ-hydroxy compound. The ratio of alpha to beta epoxides in XI, and hence the eventual ratio of IIα and IIβ alcohols in XII, produced from starting material X is dependent in large measure on the nature of $R_5$ in X. Recall that G is defined as

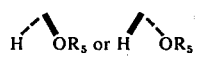

wherein $R_5$ is hydrogen, acetyl, or —Si—(A)$_3$ wherein A is as defined above. For either definition of G, i.e., R configuration or S configuration, when $R_5$ is hydrogen, more Formula-XI beta epoxide is formed than when $R_5$ is acetyl, and more Formula-XI beta epoxide is formed when $R_5$ is acetyl than when $R_5$ is —Si—(A)$_3$. For example, when G in formula X is

the preferred basic hydrogen peroxide epoxidation gives about equal amounts of alpha and beta epoxides, but when G in formula X is

about 3 parts of alpha epoxide and one part of beta epoxide are obtained, and when G in formula X is

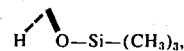

about 4 parts of alpha epoxide and one part of beta epoxide are obtained, both reactions with the same epoxidation reagent. When G in formula X is

about one part of alpha epoxide and 3 parts of beta epoxide are obtained with basic hydrogen peroxide, but when G is

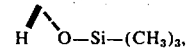

about 6 parts of alpha epoxide and 4 parts of beta epoxide are obtained with the same epoxidation reagent.

Each of the novel Formula-V and -VI compounds of this invention has a hydroxy attached in beta configuration to the cyclopentane ring. Some of the compounds of Formula V, i.e., when Y is

are encompassed by Formula XII (Chart A). The other Formula-V compounds and all of the Formula VI compounds are prepared as described below from Formula-XII compounds wherein the hydroxy at C-11 is attached in beta configuration. Therefore, when a Formula-V or Formula-VI compound is described as a final product for pharmacological purposes, there is advantage in choosing a corresponding Formula-X starting material which gives the maximum amount of beta epoxide during the transformation of X to XI. Those will be the Formula-X compounds wherein G is

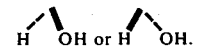

On the other hand, when a prostanoic acid product with the natural 11α configuration for the hydroxy at C-11 is the desired final product, e.g., PGE$_2$, PGF$_2$ α, or PGF$_2$ β, there is advantage in choosing a Formula-X starting material which gives a greater amount of the alpha epoxide during the transformation of X to XI. Those would be Formula-X compounds wherein X is

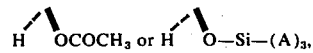

or the corresponding 15(S) compounds.

As mentioned above, the starting material of Formula X encompass not only the Formula-VIII and -IX compounds obtained from *Plexaura homomalla* but also the silyl compounds of Formula X$_a$. When desired as reactants, these silyl compounds are prepared by silylation of PGA$_2$, 15β-PGA$_2$, or the methyl esters of those. These silylations are carried out by procedures known in the art. See, for example, Pierce, "Silylation of Organic Compounds", Pierce Chemical Co., Rockford, Ill. (1968). The C-15 hyroxy group of PGA$_2$, 15β-PGA$_2$, or their methyl esters is transformed to an —O—Si—(A)$_3$ moiety wherein A is as defined above, sufficient silylating agent be ng used according to known procedures to accomplish that. The necessary silylating agents for this purpose are known in the art or are prepared by methods known in the art. See, for example, Post, "Silicones and Other Organic Silicon Compounds," Reinhold Publishing Corp., New York, N.Y. (1949). In the case of PGA$_2$ and 15β-PGA$_2$, excess silylating agent and prolonged treatment also transform the —COOH to —COO—Si—(A)$_3$. It is optional in transforming X to XI whether or not this —COOH of PGA$_2$ or 15β-PGA$_2$ is esterified to —COO—Si—(A)$_3$, since that ester group is transformed to —COOH during formation and isolation of the Formula-XI epoxide product.

The various A's of a —Si—(A)$_3$ are alike or different. For example, an —Si—(A)$_3$ can be trimethylsilyl, dimethylphenylsilyl, or methylphenylbenzylsilyl.

When it is desired to retain the —Si—(A)$_3$ moiety at C-15 in the Formula-XI epoxide product, for example, to give steric control in a subsequent reaction, it is important in isolating the epoxide that the presence of acid be avoided and that contact with water be minimized unless the water is kept cold, i.e., below about 10° C.

Referring again to Chart A, the transformation of epoxide XI to hydroxy compound XII is accomplished by reduction with chromium (II) salts, e.g., chromium (II) chloride or chromium (II) acetate. Those salts are prepared by methods known in the art, e.g., Inorganic Syntheses, VIII, 125 (1966); ibid., VI, 144 (1960); ibid. III, 148 (1950); ibid. I, 122 (1939); and references cited in those. This reduction is carried out by procedures known in the art for using chromium (II) salts to reduce epoxides of αβ-unsaturated ketones to β-hydroxy letones. See, for example, Cole et al., J. Org. Chem. 19, 151 (1954), and Neher et al., Helv. Chem. Acta 42, 132 (1959). In these reactions, the absence of air and strong acids is desirable. If it is desired to maintain a —Si—(A)$_3$ moiety on C-15, a neutral reaction mixture is preferred. An especially preferred procedure is to generate the chromium (II) ion in the presence of the Formula-XI epoxide, for example, by mixing the epoxide with a chromium (III) salt, e.g., the chloride, with metallic zinc in the presence of acetic acid. The desired Formula-XII compound is isolated from the reduction reaction mixture by methods known in the art, care being taken to minimize contact of the product with acid and water, especially warm water, when retention of a —Si—(A)$_3$ at C-15 is desired.

Unexpectedly, amalgamated aluminum metal has also been found to be useful as a reducing agent in place of chromium (II) salts to transform Formula XI epoxides to Formula XII hydroxy compounds. This reagent was previously not known to be useful for this type of reaction. This use of amalgamated aluminum represents a distinct and separate aspect of this invention.

Amalgamated aluminum is prepared by procedures known in the art, for example, by contacting aluminum metal in the form of foil, thin sheet, turnings, or granules with a mercury (II) salt, for example, mercuric chloride, advantageously in the presence of sufficient water to dissolve the mercury (II) salt. Preferably, the surface of the aluminum metal is free of oxide. That is readily accomplished by physical removal of the usual oxide layer, e.g., by abrasion or scraping, or chemically, e.g., by etching with aqueous sodium hydroxide solution. It is only necessary that the aluminum surface be amalgamated. The amalgamated aluminum should be freshly prepared, and maintained in the absence of air and moisture until used.

The reductive opening of the Formula-XI epoxide ring is accomplished by contacting said epoxide with the amalgamated aluminum in the presence of a hydroxylic solvent and sufficient inert organic liquid diluent to give a mobile and homogeneous reaction mixture with respect to the hydroxylic solvent and said epoxide. Among hydroxylic solvents, water is especially preferred although lower alkanols, e.g., methanol and ethanols are also operable.

Examples of inert organic liquid diluents are normally liquid ethers such as diethyl ether, tetrahydrofuran, dimethoxyethane, diglyme (dimethyl ether of diethylene glycol), and the like. Especially preferred is tetrahydrofuran. When a water-immiscible liquid diluent is used, a mixture of water and methanol or ethanol is especially useful in this reaction since the latter two solvents also aid in forming the desired homogeneous reaction mixture. For example, a mixture of diethyl ether and water is used with sufficient methanol to give a homogeneous reaction mixture.

This reductive opening requires two hydrogen atoms per molecule of epoxide. Amalgamated aluminum reacts readily with water and more slowly with other hydroxylic solvents to given hydrogen. One atomic equivalent of aluminum required 3 molecular equivalents of the hydroxylic so vent to give 3 atomic equivalents of hydrogen. Therefore, one molecular equivalent of epoxide requires two-thirds atomic equivalent of aluminum and two molecular equivalents of the hydroxylic solvent. Evolution of hydrogen gas (H$_2$ molecules) is observed during this reductive opening of the epoxide. It is not known whether the reductive opening is caused by hydrogen atoms or hydrogen molecules. However, some of the hydrogen gas escapes from the reaction mixture. Therefore, it is preferred to use an excess of amalgamated aluminum and hydroxylic solvent, preferably at least one atomic equivalent of aluminum and three molecular equivalents of hydroxylic solvent per molecular equivalent of epoxide. Because of the relatively high economic value of the epoxide compared with amalgamated aluminum and hydroxylic solvents, it is preferred to assure maximum yields of the desired Formula-XII hydroxy compound by use of substantially greater excess of amalgamated aluminum and hydroxylic solvent, e.g., up to ten times or more of those reagents than is theoretically required.

The reductive opening of the epoxide is carried out by mixing a solution of the epoxide in the organic diluent with the amalgamated aluminum and the hydroxylic solvent. Since the reaction is exothermic, it is usually advantageous to cool the solution to a low temperature, e.g., −20° C. to 0° C., before adding the amalgamated aluminum and hydroxylic solvent and to maintain the reaction mixture in the range 20° to 30° C. by external cooling. This is especially advantageous when water is used as the hydroxylic solvent. Higher reaction temperatures are operable but not preferred when a high yield of the Formula-XII products is desired. Stirring is preferred during the reaction since the reaction mixture is heterogeneous with respect to the solution and the amalgamated aluminum.

For reasons not understood, better yields and a shorter reaction time are usually observed when only part of the amalgamated aluminum is added at the start of the reaction, additional portions being added during the reaction, e.g., at one-hour intervals, than when the entire amount of amalgamated aluminum is added at the start of the reaction. A suitable procedure is to add about one-third of the amalgamated aluminum at the start, about one-third of the amalgamated aluminum at the start, about one-third after one hour, and another third after a second hour. The course of the reaction is advantageously determined by withdrawing small portions of the solution and determining the presence or absence of starting material by thin layer chromatography. For example, when $R_2$ is methyl and G is

in Formulas XI and XII, a suitable TLC system is ethyl acetate-cyclohexane-acetic acid (40/60/2), the Formula-XI starting material having $r_f$ 0.64, and the two Formula-XII products having $r_f$ 0.25 (II$\beta$) and $r_f$ 0.20 (II$\alpha$).

As a modification of the above-described process for reductive opening of the epoxide, it has been found quite unexpectedly that instead of employing a Formula-XI compound wherein $R_2$ is hydrogen, the reductive opening reaction proceeds more smoothly and completely if there is used, instead, an epoxide of the formula

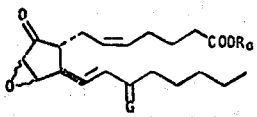   XIa wherein G and

are as defined above and $R_6$ is a cation of an alkali or alkaline earth metal or a quaternary ammonium group.

Thus, the Formula-XI epoxide compound is treated with a hydroxide or oxide of lithium, sodium, potassium, magnesium, calcium, barium, or strontium prior to contacting with the aluminum amalgam. Optionally, the quaternary ammonium bases are used for this neutralization, for example benzyltrimethylammonium hydroxide. The base is used in equivalent amount to the acid so that $R_5$ is replaced by the corresponding metal or quaternary ammonium cation. Alternatively, instead of the hydroxides or oxides, there are employed the hydrides, the carbonate, the bicarbonates, or the alkoxides, for example lithium hydride, potassium carbonate, sodium bicarbonate, magnesium methoxide, and the like, which form the corresponding Formula-XI$a$ salts with the Formula-XI free acid. Alternatively, a metal or quaternary-ammonium carboxylate compound or Formula-XI$a$ salt carried forward from the epoxidation step, whether isolated in that step or not, is employed in the reductive step with aluminum amalgam. It is preferred that the Formula-XI$a$ salt be soluble in the organic diluent-alkanol-water or organic diluent-water medium used for the reduction step. By using the above-described salts, the reduction step proceeds smoothly without formation of insoluble aluminum salts which hinder the reaction. Following the reduction or hydrolysis step, the $R_6$ cations are replaced with hydrogen by means known in the art, for example by acidification and extraction of the acid compound into an organic phase.

The desired Formula-XII hydroxy products are isolated by filtration of the reaction mixture, advantageously after addition of magnesium sulfate as a filter aid, and evaporation of the organic diluents. The Formula-XII products are then hydrolyzed if desired to remove $-Si-(A)_3$ from C-15, and the II$\alpha$ and II$\beta$ products of Formula XIII are separated, if desired, by procedures known in the art, e.g., chromatography on silica gel.

The products of Formula-XII are all of the PGE$_2$-type and include PGE$_2$, PGE$_2$ 15-acetate, PGE$_2$ methyl ester, PGE$_2$ 15-acetate methyl ester, PGE$_2$ and PGE$_2$ methyl ester with an $-O-Si-(A)_3$ at C-15, the corresponding 15$\beta$ compounds, and compounds corresponding to all of those wherein hydroxy is attached to C-11 in beta configuration.

As mentioned above, the transformation of X to XI to XII usually gives a mixture of Formula-XII PGE-type products, part with alpha and part with beta configuration for the hydroxy at C-11. There are several alternatives regarding that mixture. If $-O-Si-(A)_3$ is attached to C-15, that can readily be transformed by hydrolysis to $-OH$. These hydrolyses are carried out by prior art procedures known to be useful for transforming silyl ethers to alcohols. See, for example, Pierce, cited above, especially p. 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary. Also, if $-O-COCH_3$ is attached to C-15, that can readily be transformed to $-OH$ by acid-catalyzed alcoholysis as described above for removing the acetyl group of the Formula-VIII and -IX PGA type starting materials. Both of those transformations are shown in Chart A, i.e., XII to XIII. Either before or after those transformations of XII to XIII, the Formula-XII or -XIII mixture of II$\alpha$ and II$\beta$ isomers can be separated by methods known in the art, advantageously by chromatography on silica gel.

Further regarding the Formula-XIII compounds, those compounds wherein the configuration of the hydroxy at C-11 is beta are within the scope of the Formula-V novel compounds of this invention, and those compounds wherein the configuration of the hydroxy at C-11 is alpha and B is

are within the scope of the Formula-VII novel compounds of this invention. Both groups of novel compounds are used for pharmacological purposes described above for those compounds, the acids also being useful as reactants to prepare pharmacologically useful esters and pharmacologically acceptable and useful salts, both as described above. Moreover, Formula-XIII compounds wherein the configuration of the hydroxy at C-11 is alpha and B is

are PGE₂ and PGE₂ methyl ester, both of known pharmacological utility.

Still further regarding the separated compounds of Formulas XII and XIII, when a compound with one configuration at C-11, either alpha or beta, is desired as an intermediate or for pharmacological purposes, the other isomer is readily dehydrated to give additional Formula-X PGA-type starting material which is then used as a starting material according to the processes defired in Chart A and procedures described above to give additional of the desired isomer. These dehydrations are accomplished by procedures known in the art for dehydration of PGE-type compounds to PGA-type compounds. See, for example, Pike et al., Proc. Nobel Symposium II, Stockholm (1966), Interscience Publishers, New York, p. 162 (1967), and British patent specification No. 1,097,533. These are acidic dehydrations, and alkanoic acids of 2 to 6 carbon atoms, inclusive, especially acetic acid, are preferred for this purpose. Dilute aqueous solutions of mineral acid, e.g., hydrochloric acid, especially in the presence of a solubilizing diluent, e.g., tetrahydrofuran, are also useful as reagents for these acidic dehydrations, although these reagents may also cause partial hydrolysis of the Formula-XII or -XIII methyl esters to carboxylic acids. A —Si—(A)₃ moiety at C-15 is also removed during all of these acidic dehydrations.

Still further regarding the Formula-XII and -XIII compounds, either as mixtures or separately, any of those is transformed to other useful compounds or mixtures by changing these PGE-type compounds to PGF-type products by reducing the ring carbonyl at C-9 to alpha hydroxy or beta hydroxy. Those transformations are shown in Chart B.

In Chart B, R₄ is hydrogen, methyl, or —Si—(A)₃, R₂ is hydrogen or methyl, R₇ is hydrogen or —Si—(A)₃, and G is

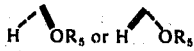

wherein R₅ is hydrogen or —Si—(A)₃ when R₄ and R₂ are hydrogen; R₅ is hydrogen, acetyl, or —Si—(A)₃ when R₂ and R₄ are methyl; and R₅ is —Si—(A)₃ when R₄ is —Si—(A)₃, wherein A is as defined above, with the proviso that when R₅ is —Si—(A)₃, R₇ is also —Si—(A)₃. Further in Chart B, B in Formula XVI is

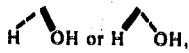

and ~ indicates attachment to the cyclopentane ring in alpha or beta position.

The Chart B starting material XII is prepared as shown in Chart A. The compounds of Formula XIII in Chart A are included in Formula XII. As described above, 15β-PGE₂,

CHART B

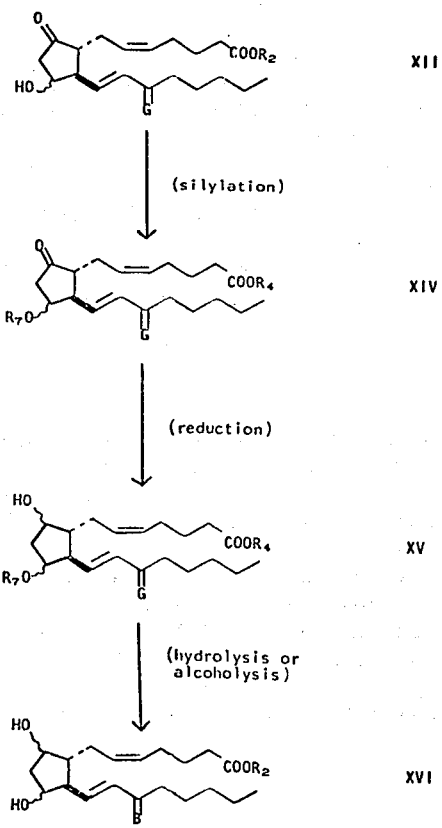

15β-PGE₂ acetate, 15β-PGE₂ methyl ester, and 15β-PGE₂ methyl ester acetate are obtained from *Plexaura homomalla* (Esper), 1792, forma R. All of those compounds are encompassed by Formula XII, and thus, extraction of this form of *Plexaura homomalla* provides an alternative source of these starting materials.

Referring to Chart B, the starting material XII can be a mixture of compounds with regard to the configuration of C-11, or the starting material can be stereochemically pure with respect to C-11, depending upon whether there has been an earlier separation of 11α and 11β isomers (see above discussion of Chart A reactions).

The transformation of PGE-type starting material XII to PGF-type product XVI involves reduction of a ring carbonyl to a ring hydroxy. This process is known in the art for some of the compounds encompassed by Formula XII, i.e., when the configuration at C-11 is alpha and the configuration at C-15 is S. For the other compounds encompassed by Formula XII, this reaction is novel, and novel Formula-XV and -XVI compounds are produced.

For this carbonyl-to-hydroxy reduction, methods known in the art are used. See, for example, Pike et al., J. Org. Chem. 34, 3552 (1969). Use is made of any of the known ketonic carbonyl reducing agents which do not reduce ester or acid groups or carbon-carbon double bonds. Examples of those are the metal borohydrides, especially sodium, potassium, lithium, and zinc borohydrides, lithium (tri-tertbutoxy) aluminum hydride, meta trialkoxy borohydrides, e.g., sodium trimethoxyborohydride, and diisobutylaluminum hydride. The sodium, potassium, and zinc borohydrides are preferred for this reduction, especially zinc borohydride.

Unexpectedly, the amalgamated aluminum metal found useful above in transforming the Formula-XI epoxides to Formula-XII hydroxy compounds has also been found useful as an agent for this carbonyl-to-hydroxy reduction of PGE-type compounds to PGF-type compounds. Either the PGE-type salts or the PGE-type esters are employed, for example the Formula-XII hydroxy compounds produced from the Formula-XI epoxides with or without intermediate isolation. Furthermore, the Formula-XI epoxides may be subjected to the combined epoxide-reduction and carbonyl-reduction reactions practically simultaneously by operating at higher temperatures, for example 40°–60° C., although it is preferred for high yields of the 11-hydroxy compounds that the reductions be done stepwise. The solvents which are operable for this reduction are generally the same as those found useful for the epoxide-reduction step. Somewhat higher temperatures or longer reaction times are required for the carbonyl-to-hydroxy reduction, however. For example, at 25° C., about 4 to 24 hours are required; at higher temperatures, e.g. 50°–60° C., about 1 to 2 hours are sufficient.

This carbonyl reduction usually produces a mixture of $PGF_\alpha$-type and $PGF_\beta$-type compounds, i.e., compounds with the alpha configuration and compounds with the beta configuration for the hydroxy at C-9. This mixture of alpha and beta isomers is separated by methods known in the art, e.g., chromatography on silica gel. See Pike et al., ibid., for example. If the Formula-XII starting material is a mixture of $11\alpha$ and $11\beta$ isomers, then this reduction will usually produce four isomers, i.e., $9\alpha, 11\alpha, 9\alpha, 11\beta, 9\beta, 11\alpha$, and $9\beta, 11\beta$. Those compounds are also separated from such mixtures by silica gel chromatography.

Regarding the transformation of XII to XIV in Chart B, it will be observed that the parameters for XII are such that all XII compounds are included in XIV. In other words, the transformation XII to XIV is an optional process step in proceeding from XII to XV. The reason for this is as follows. During the reduction of XIV to XV, the ratio of 9α-hydroxy and 9β-hydroxy compounds formed will be different when $R_7$ in XIV is hydrogen than when $R_7$ is $-Si-(A)_3$. For example, with the Formula-XIV compound wherein $R_4$ is hydrogen, G is

and $R_7O\sim$ represents HO---, i.e., 11α-hydroxy, sodium borohydride reduction gives 42 parts of the corresponding Formula-XV 9α-hydroxy compound, and 58 parts of the 9β-hydroxy compound. But with the Formula-XIV compound wherein $R_4$ is hydrogen, G is

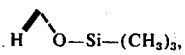

and $R_7O\sim$ represents $(CH_3)_3-Si-O-$, sodium borohydride reduction gives 85 parts of the corresponding Formula-XV 9α-hydroxy compound and 15 parts of the 9β-hydroxy compound. Similar differences are observed with the other isomers encompassed by Formula XIV although not necessarily in the same direction. Accordingly, whether $R_7$ in Formula XIV is to be hydrogen or $-Si-(A)_3$ depends on the particular formula XV C-9 isomer desired and the influence of silylation on the isomer ratio. For any particular Formula-XIV starting material, the latter is readily determined by small scale reduction with and without silylation. When silylation before carbonyl reduction is indicated, largely for economic reasons, it is preferred that A be methyl, i.e., that $R_7$ be $(CH_3)_3-Si-$.

This transformation of XII to XIV wherein Ry is $-Si-(A)_3$ is carried $R_7$ as described above for the transformation of hydroxy to $-O-Si-(A)_3$ at C-15 prior to the Chart A reactions. When $R_2$ in XII is hydrogen, the $-COOH$ is also transformed in part or entirely to $-COO-Si-(A)_3$ with prolonged silylation and excess silylating agent. It is optional in transforming XII to XIV wherein $R_7$ is $-Si-(A)_3$ whether or not the -COOH of XII is esterified to $-COO-Si-(A)_3$. When G in formula XIV is

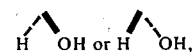

those $-OH$ are also transformed to $-O-Si-(A)_3$ by this silylation.

With regard to the Formula-XV carbonyl reduction product (Chart B), when the method used to isolate said product does not remove any $-Si-(A)_3$ groups which may be present, that is accomplished as described above for the removal of $-Si-(A)_3$ groups from Formula-XII products (Chart A, XII to XIII). Also, when G in Formula XV is

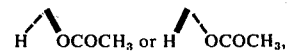

the acetyl is removed by alcoholysis also as described above for changing acetoxy at C-15 to hydroxy. These reactions are shown in Chart B as XV to XVI.

When $R_2$ in Formula XVI is methyl and the compound wherein $R_2$ is hydrogen is desired, that methyl ester is saponified, by methods known in the art. See, for example, Just et al., J. Am. Chem. Soc. 91, 5371 (1969). This saponification also changes a C-15 acetate to a C-15 hydroxy.

The compounds encompassed by Formula XVI include the known compounds $PGF_{2\alpha}$, $PGF_{2\beta}$, and the methyl esters of those. Also included in Formula XVI are the novel compounds 15β-$PGF_{2\alpha}$, 15β-$PGF_{2\beta}$, and the methyl esters of those. All of these new and old compounds are 11α-hydroxy compounds. Also included in Formula XVI are the corresponding but novel 11β-hydroxy compounds which are also encompassed by Formula V and which are useful for the pharmacological purposes described above either as such or transformed into salts or esters as described above.

When one of these Formula-XVI compounds has the R or epi configuration for the hydroxy at C-15, and the corresponding compound with the S configuration at C-15 is desired, or when one of these Formula-XVI compounds has the S configuration for the hydroxy at C-15, and the corresponding compound with the R or epi configuration at C-15 is desired, those desired compounds are made by the processes of Chart C. In Chart C, $R_2$, $R_4$, $R_7$, B, and $\sim$ are as defined above.

The overall process scheme of Chart C is to start with one particular C-15 isomer of a compound encompassed by Formula XVI, i.e., either 15(S) or 15(R). The C-15 hydroxy of that isomer is oxidized to a ketonic carbonyl (XVII). Then, after an optional silylation of the C-9 and C-11 hydroxy groups (XVIII), the C-15 carbonyl is reduced back to a secondary hydroxy group. That reduction produces two C-15 hydroxy isomers, one with S configuration and one with R or epi configuration. After removal of any silyl groups, the isomers XIX and XX are separated. One of the isomers will be the same compound used as starting material (XVI). The other isomer will be the desired product. The starting material isomer is recycled to produce more of the desired isomer. This reaction scheme has previously been used to transform $PGF_{1\alpha}$ to $15\beta$-$PGF_{1\alpha}$. See Pike et al., J. Org. Chem. 34, 3552 (1969).

Referring now to Chart C, starting material XVI (from

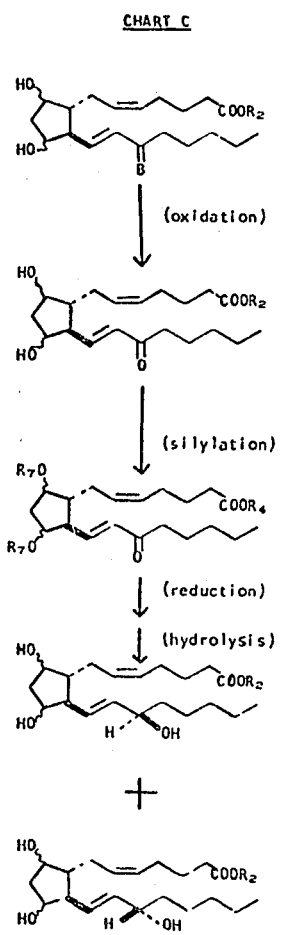

Chart B) is a single compound, a mixture of two compounds, one with alpha and one with beta configuration at C-9, or a mixture of four compounds, i.e., $9\alpha,11\alpha$, $9\alpha,11\beta$, $9\beta,11\alpha$, and $9\beta,11\beta$.

For the oxidation of XVI to XVII, any oxidizing agent can be used which will oxidize an allylic alcohol to an $\alpha,\beta$-unsaturated ketone or aldehyde. Examples of those are 2,3-dichloro-5,6-dicyano-1,4-benzoquinone, activated manganese dioxide, or nickel peroxide (see Fieser et al., "Reagents for Organic Syntheses,"John Wiley & Sons, Inc., New York, N.Y., 1967, pp. 215, 657, and 731). Alternatively, these oxidations are carried out by oxygenation in the presence of the 15-hydroxyprostaglandin dehydrogenase of swine lung (see Arkiv for Kemi 25, 293 (1966)). These reagents are used according to procedures known in the art. See, for example, J. Biol. Chem. 239, 4097 (1964).

Regarding the transformation of XVII to XVIII in Chart C, it will be observed that the parameters for XVIII are such that all XVII compounds are included in XVIII. In other words, the transformation of XVII to XVIII is an optional process step in proceeding from XVII to XIX and XX. The reason for this is as follows. During the reduction of XVIII to XIX and XX, the ratio of XIX to XX obtained will be different when $R_7$ in XVIII is hydrogen than when $R_7$ is $-Si-(A)_3$. For example, reduction of the Formula-XVIII $9\alpha,11\alpha$-isomer wherein $R_4$ and $R_7$ are both hydrogen with zinc borohydride gives the corresponding Formula-XIX and -XX in the amounts 43 parts of XIX (R or epi configuration) and 57 parts of XX (S configuration). On the other hand, when $R_7$ in the Formula-XVIII reactant is $-Si-(A)_3$, the amounts with the same reducing agent are 27 parts of XIX and 73 parts of XX. Similar differences are observed with the other isomers encompassed by Formula XVIII although not necessarily in the same direction. Accordingly, whether $R_7$ in formula XVIII is to be hydrogen or $-Si-(A)_3$ depends on the particular C-15 isomer desired and the influence of silylation on the isomer ratio. For any particular Formula-XVII starting material, the latter is readily determined by small scale reductions with and without silylation. When silylation before carbonyl reduction is indicated, largely for economic reasons, it is preferred that A be methyl, i.e., that $R_7$ be $(CH_3)_3-Si-$.

These silylations are carried out as described above for the Chart A and Chart B silylation.

The carbonyl reduction of XVIII to XIX is carried out as described above for the transformation of PGE-type Formula-XIV compounds to PGF-type Formula-XV compounds. As for those reductions, the sodium, potassium and zinc borohydrides are preferred as reducing agents, especially zinc borohydride.

When the method used to isolate the carbonyl reduction product does not remove any $-Si-(A)_3$ groups which may be present, that is accomplished as described above for the removal of $-Si-(A)_3$ groups from Formula-XII products (Chart A, XII to XIII).

The Formula-XIX and -XX products are separated from each other by methods known in the art, for example, silica gel chromatography. See, for example, Pike et al., J. Org. Chem. 34, 3552 (1969) for this type of separation.

If one of the isomers or isomer mixtures of Formulas XIX or XX is not desired for a pharmacological use as such or transformed to esters or pharmacologically acceptable salts as described above, that isomer or isomer mixture is recycled as a Formula-XVI starting material in the processes of Chart C to produce additional of the desired isomer.

The products of Formulas XIX and XX wherein the configuration of the C-11 hydroxy is beta are encompassed by Formula V. The products of Formula XIX wherein the configuration of the C-11 hydroxy is alpha are encompassed by Formula VI. The intermediates of Formula XVII are encompassed by Formula VII. Thus, all of the compounds are useful for the pharmacological purposes described above for the Formula V, VI and VII compounds. The compounds prepared as in Chart C are also useful to make the other esters and the pharmacologically acceptable salts of the Formula V, VI, and VII compounds also as described above.

There are two particular embodiments of the novel process of this invention which are especially preferred. One of those embodiments provides an optional route to PGF$_{2\alpha}$, and starts with 15$\beta$-PGA$_2$ acetate methyl ester, the most abundant component of Plexaura homomalla (Esper), 1792, forma R. The other embodiment provides a preferred route of PGE$_2$, and starts with PGA$_2$, readily obtained as described above by maintaining colonies or colony pieces of Plexaura homomalla (Esper), 1792, forma S in contact with water in a temperature range up to 50° C. until substantially free of PGA$_2$ 15 acetate methyl ester.

The first of these embodiments is shown in Chart D, and the second is shown in Chart E. All of these Chart D and Chart E reactions and reagents for effecting them are

CHART D

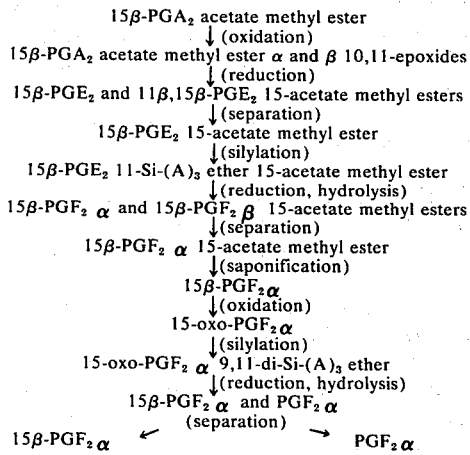

CHART E

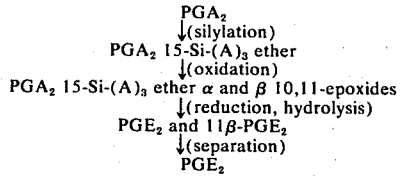

described generically and specifically above, and all are exemplified below. In Charts D and E, it is preferred that —Si—(A)$_3$ be —Si—(CH$_3$)$_3$. Also in Charts D and E it is optional whether silylation of 15-oxo-PGF$_{2\alpha}$ (Chart D) or PGA$_2$ (Chart E) produces the corresponding —Si—(A)$_3$ ester-ether or only the ether.

The invention is more fully understood by the following Examples and Preparations:

All temperatures are in degrees centigrade.

Ultraviolet spectra are recorded on a Cary Model 15 spectrophotometer.

The collection of chromatographic eluate fractions starts when the eluant front reaches the bottom of the column.

"Brine", herein, refers to aqueous saturated sodium chloride solution.

The A-IX solvent system used in thin layer chromatography (TLC) is made up from ethyl acetate-acetic acid-2,2,4-trimethylpentane-water (90:20:50:100) according to M. Hamberg and B. Samuelsson, J. Biol. Chem. 241, 257 (1966).

Preparation 1

To distinguish Plexaura homomalla (Esper), 1792, forma R from Plexaura homomalla (Esper), 1792, forma S, a TLC method is used. A specimen approximately 2 cm. in length is harvested and placed in a small vial, with a small amount of water if necessary to insure it is wet, and kept closed for 6–24 hrs. About one ml. of methanol is then added and the sample is either shaken for 2 hrs. at about 25° C. or is stored for 16–24 hrs. at about 10° C. A sample of the liquid (10–21 1) is spotted on a TLC plate. It is preferred to use a fluorescent-treated silica gel plate, e.g. Uniplate Silica Gel GF (Analtech, Inc., Newark, Del.). As reference standards, spots of PGA$_2$ and 15$\beta$-PGA$_2$ are also applied. The plate is developed in the A-IX system (Hamberg and Samuelsson, J. Biol. Chem. 241, 257 (1965)). The spots are finally visualized with vanillin-phosphoric acid spray (McAleer, Arch. Biochem. E. Biophys. 66, 120 (1957)). Comparison of the unknown with the two reference spots is then made and the identity of the coral established (forma S corresponding to PGA$_2$, forma R to 15$\beta$-PGA$_2$).

Preparation 2

PGA$_2$ from Plexaura homomalla (Esper), 1792 forma S.

Colonies of Plexaura homomalla (Esper), 1792, forma S, collected from reefs off the north shore of Jamaica, are frozen by contact with solid carbon dioxide within 1 hour after removal from the reef waters. The frozen colonies are maintained in insulated boxes containing solid carbon dioxide (temperature below about —20° C.) until ready for thawing. Then, the frozen colonies (700 g.) are ground to a small particle size (Waring blender) and mixed with 1500 ml. of water. The mixture is maintained about 20 hrs. at about 25° C. with stirring. Then, the mixture is filtered through a pad of diatomaceous earth, and the filtrate is acidified with concentrated hydrochloric acid to pH about 2–3. The acidified filtrate is extracted four times with ethyl acetate. The extracts are combined, filtered, washed with brine, dried with anhydrous sodium sulfate, and evaporated under reduced pressure to give 11 g. of oily residue.

The solid residue on the ciatomaceous earth filter pad is stirred 2 hours in methanol (enough to cover said residue) at 25° C. The mixture is then filtered, and the filtrate is evaporated to give 14 g. of oily residue.

The two oily residues are combined and chromatographed on 1500 g. of acid-washed silica gel, eluting successively with 8 l. of a 25 to 65% gradient of ethyl acetate in Skellysolve B, 8 l. of a 65 to 100 % gradient of ethyl acetate in Skellysolve B, and 5 l. of 2% methanol in ethyl acetate, collecting 500 ml. fractions. (Skellysolve B is a mixture of isomeric hexanes). Fractions 8-12 are combined and evaporated to give a small amount of PGA$_2$ containing a trace of PGA$_2$ methyl ester. Fractions 15–18 are combined and evaporated to give 9.54 g. of PGA$_2$. Fractions 35–40 are combined to give 0.414 g. of PGE$_2$.

Preparation 3

15$\beta$-PGA$_2$ from Plexaura Homomalla (Esper), 1792, forma R.

Colonies of Plexaura homomalla (Esper), 1792, forma R, collected from reefs off the southeast shore of Florida near Miami, are chopped into chunks several inches long. The chunks are frozen by contact with solid carbon dioxide with one hour after removal from the reef waters. The frozen colony pieces are maintained in insulated boxes containing solid carbon dioxide (temperature below about −20° C.) until ready for thawing. Then, colony pieces (600 g.) are mixed with 1500 ml. of water. The mixture is stirred and maintained at 25° C. for 23 hours. The mixture is then filtered through a pad of diatomaceous earth, and the filtrate is acidified to pH about 2–3 with concentrated hydrochloric acid. The acidified filtrate is extracted four times with ethyl acetate. The extracts are combined, filtered, washed with brine, dried with anhydrous sodium sultate, and evaporated to give 9.2 g. of oily residue.

The solid residue on the diatomaceous earth pad is stirred 15 hours in methanol (enough to cover said residue) at 25° C. The mixture is then filtered, and the filtrate is evaporated. The residue is dissolved in ethyl acetate, and the solution washed successively with 3 N hydrochloric acid and brine, dried with anhydrous sodium sulfate, and evaporated to give 5.83 g. of an oily residue.

The second oily residue and 8.2 g. of the first oily residue are combined and chromotographed on one kg. of acidwashed silica gel, eluting successively with 3-l. portions of 25%, 35%, 45%, 55%, and 65% ethyl acetate in Skellysolve B, collecting 500-ml. fractions. Fractions 18–22 are combined and evaporated to give 5.54 g. of $15\beta$-PGA$_2$. Fractions 15–17 are combined and evaporated to give 1.37 g. of $15\beta$-PGA$_2$ methyl ester.

Preparation 4

PGA$_2$ compounds from *Plexaura homomalla* (Esper), 1792, forma S.

Frozen colonies of *Plexaura homomalla* (Esper), 1792, forma S (see Preparation 2) are broken manually into pieces several cm. in length. The pieces (500 g.) are then covered with methanol and the mixture is maintained for 3 hours at 25° C. The mixture is then ground in a Waring blender and filtered, and the filtrate is evaporated under reduced pressure. The residue is dissolved in ethyl acetate, and the solution is washed successively with one N hydrochloric acid, water, and brine, dried with anhydrous sodium sulfate, and evaporated under reduced pressure. The oily residue is chromatographed on 2 kg. of acid-washed silica gel wet-packed with Skellysolve B (a mixture of isomeric hexanes), eluting with 24 l. of a 25 to 100% ethyl acetate in Skellysolve B gradient. The fractions which contain PGA$_2$ acetate methyl ester, PGA$_2$ acetate, PGA$_2$ methyl ester, and PGA$_2$ as shown by TLC with the A-IX system are separately combined and evaporated to give those compounds.

Preparation 5

$15\beta$-PGA$_2$ compounds from *Plexaura homomalla* (Esper), 1792, forma R.

Colonies of *Plexaura homomalla* (Esper), 1792, forma R, collected from reefs off the southeast shore of Florida near Miami, are chopped into chunks several inches long. The chunks are frozen by contact with solid carbon dioxide within one hour after renoval from the reef waters. The frozen colony pieces are maintained in insulated boxes containing solid carbon dioxide (temperature below about −20°C.) until the time for extraction. Then, the frozen colony pieces are ground to a small particle size (Mitts and Merrill hogger; average largest dimension about 5 mm). The particles (1500 g.) are then stirred at high speed with 5 gallons of dichloromethane for 20 minutes at about 25° C. external temperature. The mixture of dichloromethane and particles is then filtered through a pad of diatomaceous earth, and the filtrate is evaporated to about a 2-liter volume at 30°C. under reduced pressure. The liquid which remains is washed with water, dried with sodium sulfate, and evaporated at 30° C. under reduced pressure.

The oily residue (60 g.) is chromatographed on 3 kg. of silica gel wet packed in Skellysolve B (a mixture of isomeric hexanes), eluting successively with a gradient of 4 l. of Skellysolve B and 4l. of 20% ethyl acetate in Skellysolve B, 27 l. of 20%, 18 l. of 50%, and 8 l. of 75% ethyl acetate in Skellysolve B, collecting 600-ml. fractions. Fractions 39–60 are combined and evaporated to give 24.3 g. of $15\beta$-PGA$_2$ acetate methyl ester. Between fractions 60 and 74 those fractions shown by TLC to contain $15\beta$-PGA$_2$ acetate are combined and evaporated to yield that compound. Fractions 74–76 are combined and evaporated to give 1.03 g. of $15\beta$-PGA$_2$ methyl ester. Fractions 83–91 are combined and evaporated to give 1.08 g. of 15-acetate methyl ester. Still later fractions shown by TLC to contain $15\beta$-PGE$_2$ methyl ester are combined and evaporated to yield that compound.

Detection of the respective compounds by TLC is done by methods known in the art, e.g. by spotting the extract fractions on a TLC silica gel plate alongside spots of the authentic compounds, developing the plate with the A-IX system, and observing which spots of the extract fractions correspond exactly to the spots of the authentic compounds.

Following the procedures of Preparation 5, but substituting *Plexaura homomalla* (Esper), 1792, forma S for the *Plexaura homomalla* (Esper), 1792, forma R of that example, there are obtained the corresponding compounds of 15(S) configuration, viz.: PGA$_2$ acetate methyl ester, PGA$_2$ acetate, PGA$_2$ methyl ester, PGA$_2$ 15-acetate methyl ester, and PGE$_2$ methyl ester.

Preparation 6

PGA$_2$ and 5,6-trans-PGA$_2$.

Separation of PGA$_2$ from 5,6-trans-PGA$_2$ is done on a chromatographic column using a silver-saturated ion-exchange resin. Preferably a macroreticular ion exchange resin is used, e.g. a sulfonated styrene-divinylbenzene copolymer having surface area of 40–50 sq. m./g., 30–40% porosity, and total exchange capacity of 4.5–5.0 meq. per gram of dry resin, for example Amberlyst 15, available from Rohm and Haas Co., Philadelphia, Pa. The acid-form resin is packed in a column, washed with warm water, and converted to the silver form by passing a 10% silver nitrate solution through the column until the effluent shows a pH of 3.5–4.0. The column is then washed with water to remove ionic silver, and finally was denatured ethanol (Type 3A). A solution of a mixture of PGA$_2$ and 5,6-trans-PGA$_2$, e.g. fractions 15–18 of Preparation 2, in ethanol is charged to the column. Elution with 3A alcohol then yields fractions which are combined according to their content of 5,6-trans-PGA$_2$ (faster-eluting) or PGA$_2$. Testing for the presence of 5,6-trans-PGA$_2$ or PGA$_2$ in the eluate is conveniently done by TLC using silver nitrate-treated silica gel plates (e.g. Analtech Uniplates dipped in saturated ethanolic silver nitrate and dried) and developing with the A-IX system. R$_f$ of PGA$_2$ is 0.45; R$_f$ of 5,6-trans-PGA$_2$ is 0.50. Combined fractions are concentrated, partitioned between dichloromethane and a little water, dried over sodium sulfate, and concentrated under reduced pressure to yield the title compounds.

For quantitatively assaying the 5,6-trans-PGA$_2$ content of mixtures of PGA$_2$ and 5,6-trans-PGA$_2$ a combination thin-layer-spectrophotometric assay is used. Silica gel-impregnated glass microfiber sheets (e.g. ITLC sheets of the Gelman Instrument Co., Ann Arbor, Michigan) are impregnated with silver nitrate, using 5% ethanolic silver nitrate and drying. Spots of 100 to 200 μg of the PGA$_2$ mixture and applied and developed in the solvent system 2,2,4-trimethylpentane: ethyl acetate: acetic acid: water (100:35:8:10, upper phase). The sheet is dried and sprayed with Rhodamine 6G (Applied Science Co., State College, Pa.) and viewed under ultraviolet light. The areas containing the cis and trans materials ($R_f$ of PGA$_2$= 0.6; $R_f$ of 5,6-trans-PGA$_2$= 0.7) are marked, then excised and eluted with methanol (1.9 ml.) and potassium hydroxide solution (0.1 ml. of 45%). After incubation at 40° for 30 min., the respective solutions are centrifuged and analyzed spectrophotometrically at 278 nm.

Following the procedure of Preparation 6, 5,6-trans 15β-PGA$_2$ is separated from 15β-PGA$_2$.

Preparation 7

PGE$_2$ and 5,6-trans-PGE$_2$

Following the procedure of Preparation 6, PGE$_2$ is separated from 5,6-trans-PGE$_2$ as follows. A solution of a mixture of PGE$_2$ and 5,6-trans-PGE$_2$ is charged to the column. Elution with 3A alcohol yields fractions which are combined according to their content of 5,6-trans-PGE$_2$ (faster eluting) or PGE$_2$. Assay for 5,6-trans-PGE$_2$ or PGE$_2$ is done by TLC as for the PGA$_2$-type compounds above. $R_f$ of PGE$_2$ is 0.13; $R_f$ of 5,6-trans-PGE$_2$ is 0.17. Combined fractions are concentrated, dried over sodium sulfate, and concentrated under reduced pressure to yield the title compounds.

Preparation 8

PGA$_2$ 15-Acetate Methyl Ester, separation from 5,6-Trans-PGA$_2$ 15-Acetate Methyl Ester.

A mixture of PGA$_2$ 15-acetate methyl ester and 5,6-trans-PGA$_2$ 15-acetate methyl ester (11.0 g., 85:15) is dissolved in 415 ml. of a solution of methanol-water-acetic acid (95-5-0.4) and mercuric acetate (6.1 g.), and let standing at about 25°C. for 30 min. Water (250 ml.) is added and the mixture extracted twice with 700 ml of Skellysolve B. The Skellysolve B phase is washed with 100 ml of 60% methanol, dried over sodium sulfate, and concentrated to an oil (4.35 g.) having a high content of 5,6-trans-PGA$_2$ 15-acetate methyl ester. The aqueous methanol phase is acidified with 32 ml. of 6 N. hydrochloric acid and the mixture is extracted with two portions of 700 ml. of Skellysolve B. The organic phase is dried over sodium sulfate and concentrated to an oil (5.53 g.) This last material is subjected to the same procedures again, using 350 ml. of the methanol-water-acetic acid and 4.6 g. of mercuric acetate. There covered from the work-up of the aqueous-methanol phase a fraction (3.92 g.) of the title compound containing only a small percentage of the 5,6-trans-PGA compound.

Following the procedure of Preparation 8, 5,6-trans-15β-PGA$_2$ 15-acetate methyl ester is separated from 15β-PGA$_2$ 15-acetate methyl ester.

In the following examples, the above-described 5,6-trans-PGE$_2$ and 5,6-trans-15β-PG$_2$ compounds are subjected to the same transformations as the PG$_2$ and 15β-PG$_2$ compounds disclosed herein and illustrated hereafter.

EXAMPLE 1

15β-PGA$_2$ Methyl Ester.

A solution of 70% aqueous perchloric acid (50 drops) in 50 drops of water is added to a solution of 15β-PGA$_2$ acetate methyl ester (2.0 g.) in 100 ml. of methanol. The mixture is stirred for 15 hours at 25° C. and then diluted with 80 ml. of water. The methanol is removed under reduced pressure, and the aqueous residue is extracted with ethyl acetate. The extract is washed successively with water and brine, dried with anhydrous sodium sulfate, and evaporated. The residue is chromatographed on 200 g. of silica gel, eluting with 2.5 l. of a gradient of 20–70% ethyl acetate in Skellysolve B (a mixture of isomeric hexanes), collecting 100-ml. fractions. Fractions 15–19 are combined and evaporated to give 727 mg. of 15β-PGA$_2$ methyl ester.

EXAMPLE 2

PGA$_2$ Methyl Ester.

A solution of 15β-PGA$_2$ methyl ester (250 mg.) in 20 ml. of anhydrous tetrahydrofuran is cooled to 0° C. in an atmosphere of nitrogen. Tributylamine (1.5 ml.) is added, and the mixture is stirred at 0° C. while adding methanesulfonyl chloride (1 ml.) dropwise. The mixture is stirred 30 minutes at 0° C. Then, 10 ml. of water is added, and the mixture is allowed to warm to 25° C. and is stirred for 1 hour. The tetrahydrofuran is evaporated under reduced pressure, and the aqueous residue is extracted with ethyl acetate. The extract is washed successively with one N hydrochloric acid, water, and brine, dried with anhydrous sodium sulfate, and evaporated. The residue is chromatographed on 30 g. of silica gel, eluting with 800 ml. of a gradient of 20–70% ethyl acetate in Skellysolve B, collecting 25-ml. fractions. Fractions 14–16 are combined and evaporated to give 58 mg. of PGA$_2$ methyl ester. Fractions 12 and 13 are combined to give 49 mg. of the starting material, 15β-PGA$_2$ methyl ester.

Following the procedure of Example 2, PGA$_2$ methyl ester is transformed to a mixture of PGA$_2$ and 15β-PGA$_2$ methyl esters, the two compounds being separated as in Example 2.

EXAMPLE 3

PGA$_2$ 15-formate and 15βPGA$_2$ 15-formate

A solution of sodium carbonate (50 mg.) in 7.5 ml. of anhydrous formic acid is added to PGA$_2$ (0.25 g.). This mixture is stirred under nitrogen at 25° C. for 2 hrs. The reaction mixture is concentrated under reduced pressure, taken up in benzene, and again concentrated under reduced pressure. The residue is chromatographed on acid-washed silica gel (e.g. Mallinokrod: Silicar CC-4), eluting with a gradient of 25–75% ethyl acetate-Skellysolve B (isomeric hexane mixture) and collecting fractions. Those fractions shown by TLC to contain the respective 15-formate compound, separated from its isomer and free of starting material and impurities, are combined and concentrated under reduced pressure to give the title compounds.

EXAMPLE 4

PGA$_2$ and 15β-PGA$_2$.

PGA$_2$ 15-formate (100 mg., Example 3) is dissolved in a mixture of 10 ml. of methanol and 2.5 ml. of saturated aqueous sodium bicarbonate solution. The solution is stirred under nitrogen at 25° C. for 2.5 hrs. Then 5 ml. of water and 2 ml. of 1 N. hydrochloric acid are added, and the solution concentrated. The aqueous residue is adjusted to pH 2–3 and extracted three times with ethyl acetate. The combined extracts are washed with water, dried over sodium sulfate, and concentrated to yield $PGA_2$.

Similarly, hydrolysis of 15β-$PGA_2$ 15-formate (Example 3) yields 15β-$PGA_2$.

EXAMPLE 5

15β-$PGA_2$ 10,11-Epoxide Acetate Methyl Ester.

Hydrogen peroxide 350 ml.; 30% aqueous) is added with stirring to a solution of 15β-$PGA_2$ acetate methyl ester (265 g.) in 5000 ml. of methanol under a nitrogen atmosphere at −20° C. Then, one N aqueous potassium hydroxide solution (50 ml.) is added gradually during 1 hour with stirring at −20° C. The mixture is stirred an additional 2 hours at −20° C. Then, one N hydrochloric acid (80 ml.) is added, and the methanol is removed under reduced pressure at 35° C. The residue is dissolved in 3000 ml. of ethyl acetate, and the solution is washed 3 times with 500-ml. portions of water. The combined water washes are extracted with 300 ml. of ethyl acetate. The two ethyl acetate solutions are combined, washed with brine, dried with anhydrous sodium sulfate and evaporated to give 2.75 g. of a mixture of the alpha and beta 10,11-epoxides of 15β-$PGA_2$ acetate methyl ester.

EXAMPLE 6

$PGA_2$ 10,11-Epoxide Methyl Ester.

Hydrogen peroxide (0.3 ml.; 30% aqueous) and one N aqueous sodium hydroxide (0.5 ml.) are added to a solution of $PA_2$ methyl ester (229 mg.) in 10 ml. of isopropyl alcohol at 0° C. After 2.5 hours at 0° C., 10 ml. of water and 1 ml. of one N hydrochloric acid are added, and the isopropyl alcohol is removed under reduced pressure. The residue is extracted with ethyl acetate. The extract is washed successively with water and brine, dried with anhydrous sodium sulfate, and evaporated. The residue is chromatographed on 30 g. of silica gel, eluting with 800 ml. of a gradient of 20–70% ethyl acetate in Skellysolve B, collecting 25-ml. fractions. Fractions 5–10 are combined and evaporated to give 136 mg. of a mixture of the alpha and beta 10,11-epoxide of $PGA_2$ methyl ester.

EXAMPLE 7

$PGA_2$ Acetate Methyl Ester α and β 10,11-Epoxides
Refer to Chart A.

A solution of $PGA_2$ 15-acetate methyl ester (1.954 g.) in 30 ml. of dimethoxyethane (DME) is cooled to −55° C. under nitrogen, and 5.25 ml. of t-butyl hydroperoxide is added. Then, 5 ml. of 0.25 N. methanolic lithium hydroxide (prepared from the mono-hydrate) is added over 100 min. After about 6 hrs. an additional 2.5 ml. of the base is added over 50 min. Finally, after about 23.5 hrs. the reaction is complete, as shown by TLC. The mixture is acidified to pH 5–6 with 1 N hydrochloric acid and is concentrated under reduced pressure. The residue is taken up in ethyl acetate, washed with brine, dried over sodium sulfate, and concentrated under reduced pressure. The product, 2.0 g., contains the title alpha and beta compounds in a ratio of 6:1, respectively, as shown by gas chromatography.

Following the procedures of Example 7, but replacing the lithium hydroxide solution with methanolic magnesium methoxide (prepared from magnesium and anhydrous methanol), there is obtained a product containing the alpha and beta epoxides in a ratio of 4:1.

Following the procedures of Example 7, but replacing the DME with a mixture of toluene-DME (10:1) and replacing the lithium hydroxide with Triton B (benzyltrimethylammonium hydroxide) in methanol, there are obtained the alpha and beta epoxides in a ratio of 7.2:1.

Following the procedures of Example 7, but replacing the DME with a mixture of toluene-DME (1:1) and holding the reaction temperature at −40° C., the product contains the alpha and beta epoxides in a ratio of 6.2:1.

Following the procedures of Example 7, the replacing the DME with tetrahydrofuran (THF) and replacing the lithium hydroxide solution with Triton B, there are obtained the alpha and beta epoxides in a ratio of 4.5:1.

EXAMPLE 8

15β-$PGE_2$ 15-Acetate Methyl Ester and 11β,15β-$PGE_2$ 15-Acetate Methyl Ester.

Granular aluminum metal (50 g.) is added to a solution pf mercuric chloride (50 g.) in 2 l. of water. The mixture is swirled until hydrogen gas evolution starts to become vigorous (about 30 seconds). Then, most of the aqueous solution is decanted, and the rest is removed by rapid filtration. The amalgamated aluminum is washed rapidly and successively with two 200-ml. portions of methanol and two 200-ml. portions of anhydrous diethyl ether. The amalgamated aluminum is then covered with anhydrous diethyl ether until used.

Methanol (250 ml.) and water (25 ml.) are added to a solution of a mixture of the alpha and beta 10,11-epoxides of 15β-$PGA_2$ acetate methyl ester (275 g.) in 2500 ml. of diethyl ether. The mixture is cooled to −10° C. and the amalgamated aluminum prepared as above from 50 g. of aluminum metal is added. The mixture is stirred and maintained at about 25° C. with external cooling. After one hour, amalgamated aluminum prepared as above from 50 g. of aluminum metal is added. After an additional hour of stirring at 25° C., amalgamated aluminum prepared as above from 50 g. of aluminum metal and also 25 ml. of water are added. After an additional hour of stirring at 25° C., 100 g. of magnesium sulfate is added as a filler aid, and the mixture is filtered. The filter cake is wasted thoroughly with dichloromethane and the combined filtrate and washings are evaporated at 25° C. under reduced pressure to give a mixture (247 g.) of 15β-$PGE_2$ 15-acetate methyl ester and 11β,15β-$PGE_2$ 15-acetate methyl ester.

Part of this mixture (210 g.) is chromatographed on 30 kg. of silica gel wet-packed with 60 l. of 25% ethyl acetate in Skellysolve B (6-inch diameter column), eluting successively with 60-l. portions of 25%, 30%, 35%, 40%, 45%, 50%, 55%, and 60% ethyl acetate in Skellysolve B, collecting 4-l., fractions. Fractions 71–76 are combined and evaporated to give 27 g. of 11β,15β-$PGE_2$ 15-acetate methyl ester. Fractions 81–98 are combined and evaporated to give 115 g. of 15β-$PGE_2$ 15-acetate methyl ester.

EXAMPLE 9

15β-$PGE_2$ 15-Acetate Methyl Ester and 11β,15β-$PGE_2$ 15-Acetate Methyl Ester.

Anhydrous sodium acetate (0.5 g.) and zinc dust (500 mg.) are added to a solution of a mixture of the alpha and beta epoxides of 15β-$PGA_2$ acetate methyl ester, prepared as in Example 5, in 5 ml. of acetic acid. This mixture is stirred at 25° C. in an atmosphere of nitrogen and cooled to about 15° C. One-half ml. of a solution of chromium III chloride hexahydrate (300 mg.) in 1 ml. of water is added, and the mixture is stirred at 0° C. for 3 hours. The mixture is then diluted with ethyl acetate, and the solution is washed successively with four portions of water, one N hydrochloric acid, sodium bicarbonate solution, and brine, dried with anhydrous sodium sulfate, and evaporated. The residue is chromatographed on 20 g. of silica gel, eluting with 600 ml. of a gradient of 20–75% ethyl acetate in Skellysolve B, collecting 25-ml. fractions. Fractions 10 and 11 are combined to give 11$\beta$,15$\beta$-PGE$_2$ 15-acetate methyl ester. Fractions 13 and 14 are combined to give 15$\beta$-PGE$_2$ 15-acetate methyl ester.

EXAMPLE 10

PGE$_2$ Methyl Ester and 11$\beta$-PGE$_2$ Methyl Ester.

Freshly prepared chromium (II) acetate (450 mg., argon atmosphere; Inorganic Syntheses, 8, 125) is added to a solution of 136 mg. of epoxides (Example 6) in a mixture of 3 ml. of acetic acid and one ml. of water in an atmosphere or argon at 0° C. The mixture is stirred at 5° C. under argon for 18 hours. Ice is then added to the mixture, and that mixture is extracted with ethyl acetate. The extract is washed successively with water, one N hydrochloric acid, sodium bicarbonate solution, and brine, dried with anhydrous sodium sulfate, and evaporated. The residue is chromatographed on silica gel (20 g.), eluting with 600 ml. of a gradient of 20–100% ethyl acetate in Skellysolve B, collecting 20 ml. fractions. Fractions 19–22 are combined and evaporated to give 27 mg. of 11$\beta$-PGE$_2$ methyl ester. Fractions 24–27 are combined and evaporated to give 5 mg. of PGE$_2$ methyl ester.

EXAMPLE 11

PGE$_2$ and 11$\beta$-PGE$_2$.

Hydrogen peroxide (0.35 ml.; 30% aqueous) is added to a solution of PGA$_2$ (200 mg.) in 5 ml. of methanol. The mixture is cooled to −20° C., and 0.75 ml. of one N aqueous sodium hydroxide solution is slowly added with stirring. After 1 hour of stirring at −20° C., 1 ml. of one N hydrochloric acid is added, and the mixture is evaporated under reduced pressure. The residue is dissolved in ethyl acetate, and the resulting solution is washed successively with water and brine, dried with anhydrous sodium sulfate, and evaporated. The residue is treated with amalgamated aluminum as described in Example 8, using 2.5 ml. diethyl ether, 0.25 ml. methanol, and 0.03 ml. water, the amalgamated aluminum being added in 2 portions. When the reduction is complete, ethyl acetate and one N hydrochloric acid are added to the reaction mixture and the mixture is separated in a separatory funnel. The ethyl acetate layer is washed successively with one N hydrochloric acid, water, and brine, dried with anhydrous sodium sulfate, and evaporated. The residue is subjected to preparative thin layer chromatography to give PGE$_2$ and 11$\beta$-PGE$_2$ in the ratio 1:2.

EXAMPLE 12

15$\beta$-PGE$_2$ and 11$\beta$,15$\beta$-PGE$_2$

Following the procedure of Example 11, 15$\beta$-PGA$_2$ is transformed to 15$\beta$-PGE$_2$ and 11$\beta$,15$\beta$-PGE$_2$, those being obtained in the ratio 1:1.

EXAMPLE 13

PGE$_2$ and 11$\beta$-PGE$_2$.

Hexamethyldisilizane (1 ml.) and trimethylchlorosilane (0.2 ml.) are added with stirring to a solution of PGA$_2$ (250 mg.) in 4 ml. of tetrahydrofuran at 0° C. under nitrogen. This mixture is maintained at 5° C. for 15 hours. The mixture is then evaporated under reduced pressure. Toluene is added and evaporated twice. Then the residue is dissolved in 6 ml. of methanol, and the solution is cooled to −20° C. Hydrogen peroxide (0.45 ml.; 30% aqueous) is added. Then, one N sodium hydroxide solution (0.9 ml.) is added dropwise with stirring at −20° C. After 2 hours at −20° C., an additional 0.3 ml. of the sodium hydroxide solution is added with stirring at −20° C. After another hour in the range −10° to −20° C., an additional 0.1 ml. of the sodium hydroxide solution is added. Then, 1.5 ml. of one N hydrochloric acid is added, and the mixture is evaporated under reduced pressure. The residue is extracted with ethyl acetate, and the extract is washed successively with one N hydrochloric acid and brine, dried with anhydrous sodium sulfate and evaporated. The residue is dissolved in 5 ml. of diethyl ether. To this solution is added 0.5 ml. of methanol and 0.1 ml. of water. Then, amalgamated aluminum made from 0.5 g. of aluminum metal as described in Example 8 is added to small portions during 3 hours at 25° C. Then, ethyl acetate and 3 N hydrochloric acid are added, and the ethyl acetate layer is separated and washed successively with one N hydrochloric acid and brine, dried with anhydrous sodium sulfate, and evaporated. The residue is chromatographed on 50 g. of acid-washed silica gel, eluting first with 400 ml. of a gradient of 50–100% ethyl acetate in Skellysolve B, and then with 100 ml. of 5% methanol in ethyl acetate, collecting 25 ml. of fractions. Fractions 9 and 10 are combined and evaporated to give 18 mg. of 11$\beta$-PGE$_2$. Fractions 17–25 are combined and evaporated to give 39 mg. of PGE$_2$.

Following the procedures of Example 13 but replacing PGA$_2$ with PGA$_2$ acetate and optionally omitting the silylation step, there are obtained the corresponding PGE$_2$ 15-acetate and 11$\beta$PGE$_2$ 15-acetate compounds.

EXAMPLE 14

PGE$_2$

Refer to Chart C.

a. Silylation. A mixture of PGA$_2$ (0.68 g.), 4 ml. of tetrahydrofuran (THF), and 1 ml of trimethylchlorosilane solution (5% in hexamethyldisilazane) is stirred under nitrogen for 2 hours, at about 25° C. Then the silylated material is concentrated by renoval of THF under reduced pressure, utilizing added benzene (10 ml.) to facilitate removal of THF.

b. Oxidation. A cold (−40° C.) solution of the above silylated material in 15 ml. of isopropyl alcohol is mixed with 1.2 ml. of 30% aqueous hydrogen peroxide, followed by 1.5 ml. of 3 N. aqueous lithium hydroxide added dropwise. The temperature is allowed to warm to about −30° C. The reaction is continued until the PGA$_2$ has been exhausted as shown by the absence of PGA$_2$ in a thin layer chromatographic (TLC) spot test using the A-IX system (Hamberg and Samuelsson, J. Biol. Chem. 241, 257 (1966). At −30° C. the reaction time is about 3–4 hrs. After completion, 5 ml. of 1 N. hydrochloric acid is added and the mixture is concentrated under reduced pressure. The residue is extracted with ethyl acetate, washed with 0.5 N. hydrochloric acid and then brine, dried over sodium sulfate, and concentrated to the epoxide.

c. Reduction and hydrolysis. A solution of the above epoxide in 20 ml. of THF and 2 ml. of methanol is stirred with 4 ml. of saturated aqueous sodium bicarbonate solution and cooled to 15° C. To the mixture is added, in portions with vigorous stirring, an aluminum amalgam made from 1 g. of powdered aluminum (Example 8). After stirring at about 25° C. for 45 min., a sample is analyzed by TLC for $PGE_2$ and epoxide. Reaction is continued if necessary. When the epoxide is no longer present, the supernatant suspension is decanted from the aluminum which is further washed with ethyl acetate. The combined decantate and washes are concentrated under reduced pressure. The residue is taken up in about 15–20 ml. of ethyl acetate and shaken with 20 ml. of 1 N. hydrochloric acid. The layers are separated, the organic phase is washed with 0.5 N. hydrochloric acid, and then brine, dried and concentrated to an oily residue of 0.837 g.

d. Separation. A solution of the above residue in a small amount of 20% ethyl acetate-Skellysolve B (isomeric hexanes) is applied to a chromatographic column of 65 g. of acid-washed silica, e.g. Mallinckrodt Silicar CC-4. Elution with a gradient of 20–100% ethyl acetate-Skellysolve B gives fractions. Those fractions which are shown by TLC to contain the desired compound are combined, and concentrated. There is obtained in separate fractions $PGE_2$, 0.5 g., and 11$\beta$-$PGE_2$, 0.05 g.

Alternatively, the oily product from c above is triturated in ethyl acetate-cyclohexane (1:1), cooled to about 10°C. and seeded to yield crystalline $PGE_2$, about 0.4 g. The mother liquor is subjected to silica gel chromatography to yield separate fractions of about 0.1 g. $PGE_2$ and 0.05 g. 11$\beta$-$PGE_2$.

EXAMPLE 15

$PGE_2$ a. Silylation. Following the procedure of Example 14, step a, $PGA_2$ (0.68 g.) is silylated and concentrated.

b. Oxidation. A cold (−40° C.) solution of the above silylated material in 3.0 ml. of isopropyl alcohol is mixed with 0.84 ml. of t-butyl hydroperoxide, followed by the addition of 0.352 g. of lithium hydroxide monohydrate. The reaction is continued at −40° C. to −20° C. for 5 hrs. Then, the pH of the mixture is adjusted to about 8.0 by adding carbon dioxide.

c. Reduction and hydrolysis. The above mixture is diluted with 20 ml. of THF and cooled to 15° C. To the mixture is added in portions with vigorous stirring, an aluminum amalgam made from 1 g. of powdered aluminum (Example 8). After stirring at about 25° C. for 45 min., a sample is analyzed by TLC for $PGE_2$ and epoxide. Reaction is continued if necessary. When the epoxide is no longer present, the supernatant suspension is decanted from the aluminum which is further washed with ethyl acetate. The combined decantate and washes are concentrated under reduced pressure. The residue is taken up in about 15–20 ml. of ethyl acetate and shaken with 20 ml. of 1 N. hydrochloric acid. The layers are separated, the organic phase is washed with 0.5 N. hydrochloric acid, and then brine, dried and concentrated to an oily residue of 0.837 g.

d. Separation. A solution of the above residue in a small amount of 20% ethyl acetate-Skellysolve B (isomeric hexanes) is applied to a chromatographic column of 65 g. of acid-washed silica, e.g. Mallinckrodt Silicar OC-4. Elution with a gradient of 20–100% ethyl acetate-Skellysolve B gives fractions. Those fractions which are shown by TLC to contain the desired compound are combined, and concentrated. There is obtained in separate fractions $PGE_2$, 0.5 g., and 11$\beta$-$PGE_2$, 0.05 g.

EXAMPLE 16

15$\beta$-$PGE_2$ 11-Si-$(CH_3)_3$ Ether 15-Acetate Methyl Ester.

Hexamethyldisilazane (100 g.) and then trimethylchlorosilane (20 g.) are added to a solution of 15$\beta$-$PGE_2$ 15-acetate methyl ester (Example 8) in 400 ml. of tetrahydrofuran with vigorous stirring at 25° C. under nitrogen. The reaction mixture is maintained in the range 20° to 25° C. by external cooling, and is stirred 2 hours under nitrogen. Then, the mixture is evaporated at 50° C. at reduced pressure. The residue is mixed with 150 ml. of toluene, and the mixture is filtered through a pad of diatomaceous earth. The filtrate is evaporated at 50° C. under reduced pressure. The residue is mixed with 150 ml of toluene, and again the toluene is removed under reduced pressure at 50° C. to give 75 g. of 15$\beta$-$PGE_2$ 11-Si-$(CH_3)_3$ ether 15-acetate methyl ester.

Following the procedure of Example 16, 11$\beta$-15$\beta$-$PGE_2$ 15-acetate methyl ester is transformed to the corresponding 11-Si-$(CH_3)_3$ ether.

Also following the procedure of Example 16, but using larger amounts of hexamethyldisilazane and trimethylchlorosilane, 15$\beta$-$PGE_2$ methyl ester, 15$\beta$-$PGE_2$, 11$\beta$,15$\beta$-$PGE_2$ methyl ester, and 11$\beta$,15$\beta$-$PGE_2$ are transformed to the corresponding 11,15-di-Si-$(CH_3)_3$ ethers.

EXAMPLE 17

15$\beta$-$PGF_2$ $\alpha$ 15-Acetate Methyl Ester and 15$\beta$-$PGF_2$ $\beta$ 15-Acetate Methyl Ester.

Sodium borohydride (1.42 g.) is added in one portion to a solution of 15$\beta$-$PGE_2$ 11-Si-$(CH_3)_3$ ether 15-acetate methyl ester (Example 16) (30.7 g.) in 500 ml. of absolute ethanol at 0° C. with stirring. The mixture is stirred at 0° C. for 3.5 hours. Then, 10 ml. of glacial acetic acid is added slowly with stirring at 0° C. Then, 100 ml. of water is added, and the mixture is allowed to warm to 25° C. with stirring, and is stirred 15 hours at 25° C. The ethanol is evaporated under reduced pressure, and the residue is mixed with 400 ml. of brine. The mixture is extracted with 3 portions of ethyl acetate (400 ml., 250 ml., and 150 ml.). The combined extracts are washed successively with two 100-ml. portions of water, 100 ml. of saturated aqueous sodium bicarbonate solution, two 100-ml. portions of brine, dried with anhydrous sodium sulfate, and evaporated under reduced pressure to give 24.5 g. of a mixture of 15$\beta$-$PGF_2$ $\alpha$ 15-acetate methyl ester and 15$\beta$-$PGF_2$ $\beta$ 15-acetate methyl ester.

EXAMPLE 18

15$\beta$-$PGF_2$ $\alpha$ and 15$\beta$-$PGF_2$ $\beta$ .

Aqueous sodium hydroxide solution (10%; 275 ml.) is added to a solution of 48 g. of a mixture of 15β-PGF$_2$ $_\alpha$ 15-acetate methyl ester and 15β-PGF$_2$ $_\beta$ 15-acetate methyl ester (Example 17) in 350 ml. of methanol at 0° C. with stirring under nitrogen. The mixture is allowed to warm to 25° C. with stirring, and is stirred 3 hours at 25° C. Then, the methanol is evaporated under reduced pressure at 35° C. The aqueous residue is cooled and extracted once with a mixture of diethyl ether and dichloromethane (1:1). Then, the aqueous residue is acidified with 260 ml. of 3 N hydrochloric acid, saturated with sodium chloride, and extracted with 3 portions of ethyl acetate (400 ml., 250 ml., and 150 ml.). The combined extracts are washed successively with two 100-ml. portions of water and two 100-ml. portions of brine, dried with anhydrous sodium sulfate, and evaporated to give 42 g. of a mixture of 15β-PGF$_2$ $_\alpha$ and 15β-PGF$_2$ $_\beta$.

EXAMPLE 19

15-Oxo-PGF$_2$ $_\alpha$ and 15-Oxo-PGF$_2$ $_\beta$.

The mixture of 15β-PGF$_2$ $_\alpha$ and 15β-PGF$_2$ $_\beta$ (42 g.) obtained as in Example 18 is dissolved in 950 ml. of dioxane. To this solution at 25° C. is added 2,3-dichloro-5,6-dicyano-1,4-benzoquinone (40° g.). This mixture is stirred 18 hours at 50° C. under nitrogen. The mixture is then cooled to 25° C. and filtered. The filter cake is washed with dichloromethane, and the combined filtrate and washing are evaporated under reduced pressure at 45° C. to give a mixture (66 g.) of 15-oxo-PGF$_2$ $_\alpha$ and 15-oxo-PGF$_2$ $_\beta$ Part of this mixture (33 g) is chromatographed on 3 kg. of acid-washed silica gel, eluting successively with 10 l. 60%, 10 l. 70%, 10 l. 80%, 20 l. 90% ethyl acetate in Skellysolve B, 15 l. ethyl acetate, and 10 l. 5% methanol in ethyl acetate, collecting 650-ml. fractions. Fractions 42–53 are combined and evaporated to give 8.3 g. of 15-oxo-PGF$_2$ $_\alpha$. Fractions 64–85 are combined and evaporated to give 3.3 g. of 15-oxo-PGF$_2$ $_\beta$.

EXAMPLE 20

PGF$_2$ $_\alpha$, and 15β-PGF$_2$ $_\beta$.

Hexamethyldisilazane (70 ml.) and trimethylchlorosilane (14 ml.) are added with vigorous stirring to a solution of 15-oxo-PGF$_2$ $_\alpha$ (3.0 g.) in 350 ml. of tetrahydrofuran at 25° C. under nitrogen. The mixture is stirred 18 hours at 25° C. under nitrogen. Then, the mixture is evaporated under reduced pressure at 50° C. Toluene (100 ml.) is added to the residue, and the mixture is filtered through a pad of diatomaceous earth. The filtrate is evaporated, and 100 ml. of toluene is added to the residue. This mixture is evaporated under reduced pressure to give the 9,11-di-Si-(CH$_3$)$_3$ ether of 15oxo-PGF$_2$ $_\alpha$.

This disilyl ether is dissolved in 20 ml. of 1,2-dimethoxyethane. Sodium borohydride (680 mg.) is suspended in 65 ml. of 1,2-dimethoxyethane at 0° C. under nitrogen. Anhydrous zinc chloride (1.23 g.) is added to this suspension, and the mixture is stirred 30 minutes at 0° C. Then, the solution of the disilyl ether is added dropwise during 10 minutes with stirring at 0° C. The resulting mixture is allowed to warm to 25° C. with stirring, and is stirred 4 hours at 25° C. Then, 30 ml. of water is added, followed by 8 ml. of glacial acetic acid. This mixture is stirred 15 hours at 25° C. The mixture is then poured into a mixture of ice and 100 ml. of 0.5 N hydrochloric acid. That mixture is saturated with sodium chloride, and then extracted with several portions of ethyl acetate. The combined extracts are washed with brine, dried with anhydrous sodium sulfate, and evaporated under reduced pressure. The residue (3.2 g.) is chromatographed on 600 g. of acid-washed silica gel, eluting successively with 5 l. of 75% ethyl acetate in Skellysolve B, 5 l. of 90% ethyl acetate in Skellysolve B, and 5 l. of a gradient of 90% ethyl acetate and 10% methanol in ethyl acetate, collecting 550-ml. fractions. Fractions 21–26 are combined and evaporated to give 543 mg. of 15βPGF$_2$ $_\alpha$. Fractions 28–36 are combined and evaporated to give 1.62 g. of PGF$_2$ $_\alpha$.

EXAMPLE 21

15β-PGF$_2$ $_\alpha$ 15-Acetate Methyl Ester and 15β-PGF$_2$ $_\beta$ 15-Acetate Methyl Ester.

Sodium borohydride (6.0 g.) is added in one portion with vigorous stirring to a solution of 15β-PGE$_2$ 11-Si-(CH$_3$)$_3$ ether 15-acetate methyl ester (77 g.) in 1500 ml. of methanol at −30° C. Then 5.0 g. sodium borohydride is added and the mixture is stirred 1 hour at −30° C., and a second hour while warming to 20° C. Then, glacial acetic acid (30 ml.) is added slowly, followed by 125 ml. of water. This mixture is stirred 15 hours at 25° c., and then evaporated under reduced pressure. The residue is C., with brine (2 volumes), and the mixture is extracted 3 times with ethyl acetate. The combined extracts are washed successively with water, sodium bicarbonate solution, and brine, dried with anhydrous sodium sulfate, and evaporated under reduced pressure to give 60 g. of a mixture of 15β-PGF$_2$ $_\alpha$ 15-acetate methyl ester and 15β-PGF$_2$ $_\beta$ 15-acetate methyl ester.

Part (21 g.) of this mixture is chromatographed on 1.8 kg. of silica gel, wet-packed in 50% ethyl acetate in Skellysolve B, eluting successively with 20 l. 50%, 20 l. 60%, and 5 l. 75% ethyl acetate in Skellysolve B, collecting 650-ml. fractions. Fractions 12–26 are combined and evaporated to give 22.0 g. of 15β-PGF$_2$ $_\alpha$ 15-acetate methyl ester. Fractions 44–61 are combined and evaporated to give 6.11 g. of 15β-PGF$_2$ $_\beta$ 15-acetate methyl ester.

EXAMPLE 22

15β-PGF$_2$ $_\alpha$.

Following the procedure of Example 18, 15β-PGF$_2$ $_\alpha$ 15-acetate methyl ester is saponified to 15β-PGF$_2$ $_\alpha$

EXAMPLE 23

15β2$_\beta$.2

Following the procedure of Example 18, 15β-PGF$_2$ $_\beta$ 15-acetate methyl ester is saponified to 15β-PGF$_2$ $_\beta$.

EXAMPLE 24

15-Oxo-PGF$_2$ $_\alpha$.

Following the procedure of Example 19, 15β-PGF$_2$ $_\alpha$ is oxidized to 15-oxo-PGF$_2$ $_\alpha$.

EXAMPLE 25

15-Oxo-PGF$_2$ $_\beta$.

Following the procedure of Example 19, 15β-PGF$_2$ $_\beta$ is oxidized to 15-oxo-PGF$_2$ $_\beta$.

EXAMPLE 26

PGF$_2$ $_\beta$ and 15β-PGF$_2$ $_\beta$.

Following the procedure of Example 20, 15-oxo-PGF$_2$ $_\beta$ is silylated and then reduced to a mixture of PGF$_{2\beta}$ and 15$\beta$-PGF$_{2\beta}$ which are separated as described for the alpha compounds in Example 20.

EXAMPLE 27

11$\beta$,15$\beta$-PGF$_{2\alpha}$ and 11$\beta$,15$\beta$-PGF$_{2\beta}$..

Following the procedures of Example 16 and 21 11$\beta$,15$\beta$-PGE$_2$ 15-acetate methyl ester is transformed to a mixture of 11$\beta$,15$\beta$PGF$_{2\alpha}$ 15-acetate methyl ester and 11$\beta$,15$\beta$-PGF$_{2\beta}$ 15-acetate methyl ester which are separated as described for the products of Example 21. Those acetate methyl esters are then separately saponified as in Example 18 to give 11$\beta$,15$\beta$-PGF$_{2\alpha}$ and 11$\beta$,15$\beta$-PGF$_{2\beta}$.

EXAMPLE 28

11$\beta$-15-Oxo-PGF$_{2\alpha}$.

Following the procedure of Example 19, 11$\beta$,15$\beta$-PGF$_{2\alpha}$ is oxidized to 11$\beta$-15-oxo-PGF$_{2\alpha}$.

EXAMPLE 29

11$\beta$-15-Oxo-PGF$_{2\beta}$.

Following the procedure of Example 19, 11$\beta$,15$\beta$-PGF$_{2\beta}$ is oxidized to 11$\beta$-15-oxo-PGF$_{2\beta}$.

EXAMPLE 30

11$\beta$-PGF$_{2\alpha}$ and 11$\beta$,15$\beta$-PGF$_{2\alpha}$.

Following the procedure of Example 20, 11$\beta$-15-oxo-PGF$_{2\alpha}$ is silylated and then reduced to a mixture of 11$\beta$-PGF$_{2\alpha}$ and 11$\beta$,15$\beta$-PGF$_{2\alpha}$ which are separated as described for the products of Example 20.

EXAMPLE 31

11$\beta$-PGF$_{2\beta}$ and 11$\beta$-15$\beta$-PGF$_{2\beta}$.

Following the procedure of Example 20, 11$\beta$-15-oxo-PGF$_{2\beta}$ is silylated and then reduced to a mixture of 11$\beta$-PGF$_{2\beta}$ and 11$\beta$,15$\beta$-PGF$_{2\beta}$ which are separated as described for the products of Example 20.

EXAMPLE 32

PGF$_{2\alpha}$ and PGF$_{2\beta}$ a. Silylation. Following the procedure of Example 14, step a PGA$_2$ (0.68 g.) is silylated and concentrated.

b. Oxidation. A cold (−40° C.) solution of the above silylated material in 15 ml. of isopropyl alcohol is mixed with 1.2 ml. of 30% aqueous peroxide, followed by 1.5 ml. of 3 N. aqueous lithium hydroxide added dropwise. The reaction is continued at about −30° C. for 4 hrs. Then, the pH of the mixture is adjusted to about 8.0 by adding carbon dioxide and the mixture is concentrated under reduced pressure.

c. Reduction and hydrolysis. The residue above is taken up in 20 ml. of THF and 2 ml. of methanol. To it is added with vigorous stirring, an aluminum amalgam made from 1 g. of powdered aluminum (Example 8). After the epoxide is no longer present as shown by TLC, the mixture is heated to 60° C. for about one hour to reduce all 9-oxo compounds to 9-hydroxy compounds. There is thereby formed a mixture containing F$_{2\alpha}$, F$_{2\beta}$, 11$\beta$-F$_{2\alpha}$, and 11$\beta$-F$_{2\beta}$ salts. The mixture is cooled and the supernatant material is decanted from the aluminum which is further washed with ethyl acetate. The combined decantate and washes are concentrated under reduced pressure. The residue is taken up in ethyl acetate and acidified, while stirring, with 20 ml. of 1 N. hydrochloric acid. The layers are separated and the organic phase is washed with 0.5 N. hydrochloric acid and then brine dried and concentrated under reduced pressure.

d. Separation. A solution of the above residue in a small amount of 20% ethyl acetate-Skellysolve B (isomeric hexanes) is applied to a chromatographic column of acid-washed silica, e.g. Mallinckrodt Silicar CC-4. Elution with a gradient of 20–100% ethyl acetate-Skellysolve B gives fractions. Those fractions which are shown by TLC to contain PGF$_{2\alpha}$ are combined and concentrated to yield PGF$_{2\alpha}$. Likewise, those fractions shown to contain PGF$_{2\beta}$, 11$\beta$-PGF$_{2\alpha}$, or 11$\beta$-PGF$_{2\beta}$ are combined and concentrated to yield those compounds, respectively.

EXAMPLE 33

PGF$_{2\alpha}$ and PGF$_{2\beta}$

Hydrogen peroxide (3.5ml., 30% aqueous) is added with stirring to a solution of PGA$_2$ acetate methyl ester (2.65 g) in 50 ml. of methanol under a nitrogen atmosphere at −20° C. Then, 5.0 ml. of 0.1 N. aqueous potassium hydroxide solution is added gradually over 1 hr. with stirring at −20° C. The mixture is stirred an additional 2 hrs. at −20° C. Then, carbon dioxide is added to the mixture to adjust the pH to about 7.0–8.0, and the mixture containing the alpha and beta 10,11-epoxides is concentrated under reduced pressure.

The above residue is taken up in 80 ml. of THF and 8 ml. of methanol, and cooled to −10° C. To the mixture is added in portions, with vigorous stirring, an aluminum amalgam made from 4 g. of powdered aluminum (Example 8). The mixture is stirred and maintained at about 25° C. with cooling. After an hour, a sample is analyzed by TLC for 10,11-epoxide of PGA$_2$ 15-acetate methyl ester and for PGE$_2$ 15-acetate methyl ester. Reaction is continued at about 25° C. until substantially no epoxide is left. The reaction mixture is then warmed to 60° C., with stirring. After one hour a sample is analyzed by TLC for PGE$_2$ 15-acetate methyl ester and 11$\beta$-PGE$_2$ 15-acetate methyl ester and for the corresponding PGE$_2$$_\alpha$ and PGE$_2$$_\beta$ compounds. Reaction is continued at 60° C. until no PGE$_2$ compounds are left. The mixture is cooled and the supernatant material is decanted from the aluminum which is further washed with ethyl acetate. The combined decantate and washes are concentrated under reduced pressure. The residue is taken up in ethyl acetate and chromatographed on silica gel, eluting with 20–100% ethyl acetate-Skellysolve B, collecting fractions. Those fractions which are shown by TLC to contain PGF$_{2\alpha}$ 15-acetate methyl ester are combined and concentrated to give that compound. Likewise, the fractions containing PGF$_{2\beta}$ 15-acetate methyl ester are combined and concentrated to give that compound.

PGF$_{2\alpha}$ and PGF$_{2\beta}$ are obtained by saponification of the above corresponding 15-acetate methyl esters. Aqueous sodium hydroxide (2.75 ml. 10%) is added to a solution of PGF$_{2\alpha}$ 15-acetate methyl ester (0.48 g.) in 10 ml. of methanol at 0° C. with stirring under nitrogen. The mixture is allowed to warm to 25° C. with stirring and is stirred 3 hrs. at 25° C. The mixture is partially concentrated under reduced pressure. The aqueous residue is cooled and extracted once with a mixture of diethyl ether and dichloromethane (1:1). The aqueous residue is acidified with about 2.6 ml. of 3 N. hydrochloric acid, saturated with sodium chloride, and extracted with ethyl acetate. The organic phase is washed with water and brine, dried with anhydrous sodium sulfate, and concentrated to PGF₂α. In a similar fashion, PGF₂β is obtained by saponification of PGF₂β 15-acetate methyl ester.

We claim:
1. The compound of the formula

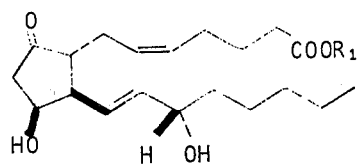

wherein $R_1$ is hydrogen, alkyl of 1 to 8 carbon atoms, inclusive, cycloalkyl of 3 to 10 carbon atoms, inclusive, aralkyl of 7 to 12 carbon atoms, inclusive, phenyl or phenyl substituted with one, 2, or 3 chloro or alkyl of 1 to 4 carbon atoms, inclusive, and the pharmacologically acceptable salts thereof when $R_1$ is hydrogen.

2. The compound according to claim 1 wherein $R_1$ is methyl.

3. The compound according to claim 1 wherein $R_1$ is hydrogen.

* * * * *